(12) United States Patent
Kobayashi et al.

(10) Patent No.: US 11,192,106 B2
(45) Date of Patent: Dec. 7, 2021

(54) FLUIDIC DEVICE, SYSTEM, METHOD OF DETECTING SAMPLE MATERIAL AND METHOD OF PURIFYING SAMPLE MATERIAL

(71) Applicant: Nikon Corporation, Tokyo (JP)

(72) Inventors: Ryo Kobayashi, Kawasaki (JP); Keiji Mitsui, Kobe (JP); Taro Ueno, Tokyo (JP); Hirofumi Shiono, Fujisawa (JP)

(73) Assignee: Nikon Corporation, Tokyo (JP)

( * ) Notice: Subject to any disclaimer, the term of this patent is extended or adjusted under 35 U.S.C. 154(b) by 209 days.

(21) Appl. No.: 16/209,857

(22) Filed: Dec. 4, 2018

(65) Prior Publication Data

US 2019/0111429 A1  Apr. 18, 2019

Related U.S. Application Data

(63) Continuation of application No. PCT/JP2017/020807, filed on Jun. 5, 2017.

(30) Foreign Application Priority Data

Jun. 6, 2016 (JP) .............................. JP2016-112689

(51) Int. Cl.
*B01L 3/00* (2006.01)
*G01N 1/34* (2006.01)
(Continued)

(52) U.S. Cl.
CPC ......... *B01L 3/502738* (2013.01); *B01J 19/00* (2013.01); *B01L 3/502715* (2013.01);
(Continued)

(58) Field of Classification Search
CPC .. B01L 3/502738; B01L 3/5027; B01L 3/502; B01L 3/50; B01L 3/502715;
(Continued)

(56) References Cited

U.S. PATENT DOCUMENTS 8,772,046 B2 * 7/2014 Fraden .............. B01L 3/502784
436/180
2004/0101444 A1 * 5/2004 Sommers ................ B01L 9/527
422/400

(Continued)

FOREIGN PATENT DOCUMENTS

EP  1792654 A2  6/2007
EP  3051293 A1  8/2016
(Continued)

OTHER PUBLICATIONS

Communication pursuant to Rule 164(1) EPC forwarding the partial supplementary European Search Report dated Nov. 15, 2019 for European Patent Application No. 17810257.0, 13 pages.
(Continued)

*Primary Examiner* — Christine T Mui
(74) *Attorney, Agent, or Firm* — Squire Patton Boggs (US) LLP

(57) ABSTRACT

A fluidic device includes a first circulation flow path and a second circulation flow path which circulate a solution containing a sample material, the first circulation flow path and the second circulation flow path share at least a part of the flow path, and at least one selected from the group consisting of a capture unit which captures the sample material, a detection unit which detects the sample material, a valve, and a pump is provided on the shared flow path.

18 Claims, 13 Drawing Sheets

(51) Int. Cl.

| | |
|---|---|
| *C12Q 1/68* | (2018.01) |
| *B01J 19/00* | (2006.01) |
| *G01N 35/08* | (2006.01) |
| *B81B 7/02* | (2006.01) |
| *C12M 1/00* | (2006.01) |
| *G01N 37/00* | (2006.01) |
| *B81B 1/00* | (2006.01) |
| *G01N 1/10* | (2006.01) |
| *B03C 1/00* | (2006.01) |
| *B03C 1/28* | (2006.01) |
| *C12N 15/09* | (2006.01) |
| *B03C 1/01* | (2006.01) |

(52) U.S. Cl.
CPC .................. *B03C 1/00* (2013.01); *B03C 1/01* (2013.01); *B03C 1/28* (2013.01); *B03C 1/288* (2013.01); *B81B 1/00* (2013.01); *B81B 1/006* (2013.01); *B81B 7/02* (2013.01); *C12M 1/00* (2013.01); *C12N 15/09* (2013.01); *C12Q 1/68* (2013.01); *G01N 1/10* (2013.01); *G01N 1/34* (2013.01); *G01N 35/08* (2013.01); *G01N 37/00* (2013.01); *B01L 2200/0621* (2013.01); *B01L 2300/088* (2013.01); *B01L 2400/04* (2013.01); *B01L 2400/06* (2013.01); *B03C 2201/18* (2013.01); *B03C 2201/20* (2013.01); *B81B 2201/054* (2013.01); *B81B 2203/0338* (2013.01)

(58) Field of Classification Search
CPC ... B01J 19/00; B03C 1/01; B03C 1/00; G01N 1/10; G01N 1/00
USPC .......................................... 422/502, 500, 50
See application file for complete search history.

(56) References Cited

U.S. PATENT DOCUMENTS

| | | | |
|---|---|---|---|
| 2009/0280475 A1* | 11/2009 | Pollack | C12Q 1/6869 435/6.11 |
| 2012/0136492 A1 | 5/2012 | Amin et al. | |
| 2012/0257470 A1 | 10/2012 | Chapron et al. | |
| 2015/0125947 A1* | 5/2015 | Korczyk | B01L 3/502746 435/289.1 |
| 2016/0199796 A1 | 7/2016 | Ichiki et al. | |

FOREIGN PATENT DOCUMENTS

| | | |
|---|---|---|
| EP | 3276359 A1 | 1/2018 |
| JP | 2006/234536 A | 9/2006 |
| JP | 2007/047110 A | 2/2007 |
| JP | 2007/101428 A | 4/2007 |
| WO | WO 02/081729 A2 | 10/2002 |
| WO | WO 2010/115123 A2 | 10/2010 |
| WO | WO 2015/046263 A1 | 4/2015 |
| WO | WO 2015/143442 A2 | 9/2015 |
| WO | WO 2015/162060 A1 | 10/2015 |

OTHER PUBLICATIONS

International Search Report dated Aug. 15, 2017 for PCT Application No. PCT/JP2017/020807, with English translation, 5 pages.
Written Opinion of the International Searching Authority dated Aug. 15, 2017 for PCT Application No. PCT/JP2017/020807, with English translation, 13 pages.
Ahrar, et al. "Microfluidic serial dilution ladder", Royal Society of Chemistry, *Analyst 2014*, vol. 139, pp. 187-190.
Hong, et al. A nanoliter-scale nucleic acid processor with parallel architecture, *Nature Biotechnology Apr. 2004*, vol. 22, No. 4, pp. 435-439.
Notice of Reasons for Rejection dated Apr. 30, 2020 for Japanese Patent Application No. 2018-522475, with English translation, 10 pages.
Communication forwarding the extended European search report dated Mar. 27, 2020 for European Patent Application No. 17810257.0, 15 pages.
Notice of Reasons for Refusal dated Sep. 26, 2019 for Japanese Patent Application No. 2018-522475, with English translation, 15 pages.

* cited by examiner

FLUIDIC DEVICE, SYSTEM, METHOD OF DETECTING SAMPLE MATERIAL AND METHOD OF PURIFYING SAMPLE MATERIAL

CROSS-REFERENCE TO RELATED APPLICATION

This is a Continuation Application of International Application No. PCT/JP2017/020807, filed on Jun. 5, 2017, which claims priority on Japanese Patent Application No. 2016-112689, filed on Jun. 6, 2016. The contents of the aforementioned applications are incorporated herein by reference.

BACKGROUND

Field of the Invention

The present invention relates to a fluidic device, a system, a method of detecting a sample material, and a method of purifying a sample material.

Background

In recent years, development of micro-total analysis systems (μ-TAS) aiming at high-speed testing, high efficiency, integration, or ultra-miniaturization of inspection equipment in the field of in-vitro diagnosis has attracted attention and been actively researched globally.

The μ-TAS is superior to conventional inspection equipment from viewpoints such as a small amount of sample can be measured and analyzed, portability and disposability at low cost.

Further, attention is being paid to the μ-TAS as a method having high usefulness in cases in which an expensive reagent is used or small amounts of multiple specimens are examined.

As a component of the μ-TAS, a device including a loop-shaped flow path and a pump disposed on the flow path has been reported (Jong Wook Hong, Vincent Studer, Giao Hang, W French Anderson and Stephen R Quake, Nature Biotechnology 22, 435-439 (2004)). In this device, a plurality of solutions are mixed in the loop-shaped flow path by injecting the plurality of solutions into the loop-shaped flow path and then operating a pump.

SUMMARY

In the field of in-vitro diagnosis, especially in point-of-care testing (POCT), it is necessary to perform multiple reactions continuously and in a short time with a small amount of sample. The μ-TAS described in Jong Wook Hong, Vincent Studer, Giao Hang, W French Anderson and Stephen R Quake, Nature Biotechnology 22, 435-439 (2004) failed to sufficiently solve this problem.

An aspect of the present invention is to provide a fluidic device which is inexpensive, can easily perform an inspection procedure including a plurality of reactions and can shorten an inspection time.

One embodiment of the present invention provides the following (1) to (6).

(1) A fluidic device according to one embodiment of the present invention includes a first circulation flow path and a second circulation flow path which circulate a solution containing a sample material, wherein the first circulation flow path and the second circulation flow path share at least a part of the flow path, and at least one selected from the group consisting of a capture unit which captures the sample material, a detection unit which detects the sample material, a valve, and a pump is provided on the shared flow path.

(2) A system according to one embodiment of the present invention includes the above-described fluidic device and a control unit which controls the opening and closing of a valve.

(3) A method of purifying a sample material according to one embodiment of the present invention is a method of purifying a sample material using a fluidic device which includes a first circulation flow path and a second circulation flow path constituted to share a part of the flow path, and in which a capture unit constituted to capture a sample material is provided on a shared flow path by the first circulation flow path and the second circulation flow path, the method including introducing a first liquid containing the sample material into the first circulation flow path, circulating and mixing the first liquid and a second liquid containing a carrier particle to be bound to the sample material in the first circulation flow path and obtaining a mixed liquid, further circulating the mixed liquid in the first circulation flow path and capturing a complex of the sample material and the carrier particle in the capture unit, removing the mixed liquid from the shared flow path, and circulating a third liquid which releases the sample material from the carrier particle in the second circulation flow path.

(4) A method of purifying a sample material according to one embodiment of the present invention is a method of purifying a sample material using a fluidic device which includes a first circulation flow path and a second circulation flow path constituted to share a part of the flow path, a capture unit constituted to capture a sample material and provided on a shared flow path by the first circulation flow path and the second circulation flow path, a loop flow path, and a bypass flow path constituted to connect together a first connecting portion and a second connecting portion that are provided in the loop flow path, and in which the first circulation flow path includes the loop flow path, and the second circulation flow path includes the bypass flow path and a flow path between the first connecting portion and the second connecting portion in the loop flow path, the method including introducing a first liquid containing the sample material into the first circulation flow path, circulating and mixing the first liquid and at least one pretreatment solution in the first circulation flow path and obtaining a first mixed liquid, circulating and mixing the first mixed liquid and a liquid containing a carrier particle to be bound to the sample material in the second circulation flow path and obtaining a second mixed liquid, further circulating the second mixed liquid in the second circulation flow path and capturing a complex of the sample material and the carrier particle in the capture unit, removing the second mixed liquid from the shared flow path, and circulating a third liquid which releases the sample material from the carrier particle in the second circulation flow path.

(5) A method of detecting a sample material according to one embodiment of the present invention is a method of detecting a sample material using a fluidic device which includes a first circulation flow path and a second circulation flow path constituted to share a part of the flow path, and in which a capture unit constituted to capture a sample material is provided on a shared flow path by the first circulation flow path and the second circulation flow path, and a detection unit constituted to detect the sample material is provided on the second circulation flow path, the method including introducing a first liquid containing the sample material into the first circulation flow path, circulating and mixing the first liquid and a second liquid containing a carrier particle to be bound to the sample material in the first circulation flow path and obtaining a mixed liquid, further circulating the mixed liquid in the first circulation flow path and capturing a complex of the sample material and the carrier particle in the capture unit, removing the mixed liquid from the shared flow path, and circulating a third liquid in the second circulation flow path and detecting the sample material in the detection unit while releasing or not releasing the sample material or a complex of the sample material and the carrier particle from the capture unit.

(6) A method of detecting a sample material according to one embodiment of the present invention is a method of detecting a sample material using a fluidic device which includes a first circulation flow path and a second circulation flow path constituted to share a part of the flow path, a capture unit constituted to capture a sample material and provided on a shared flow path by the first circulation flow path and the second circulation flow path, a detection unit constituted to detect the sample material and provided on the second circulation flow path, a loop flow path, and a bypass flow path constituted to connect together a first connecting portion and a second connecting portion that are provided in the loop flow path, and in which the first circulation flow path includes the loop flow path, and the second circulation flow path includes the bypass flow path and a flow path between the first connecting portion and the second connecting portion in the loop flow path, the method including introducing a first liquid containing the sample material into the first circulation flow path, circulating and mixing the first liquid and at least one pretreatment solution in the first circulation flow path and obtaining a first mixed liquid, circulating and mixing the first mixed liquid and a liquid containing a carrier particle to be bound to the sample material in the second circulation flow path and obtaining a second mixed liquid, further circulating the second mixed liquid in the second circulation flow path and capturing a complex of the sample material and the carrier particle in the capture unit, removing the second mixed liquid from the shared flow path, and circulating a third liquid in the second circulation flow path and detecting the sample material in the detection unit while releasing or not releasing the sample material or a complex of the sample material and the carrier particle from the capture unit.

DESCRIPTION OF EMBODIMENTS

Figure 1:
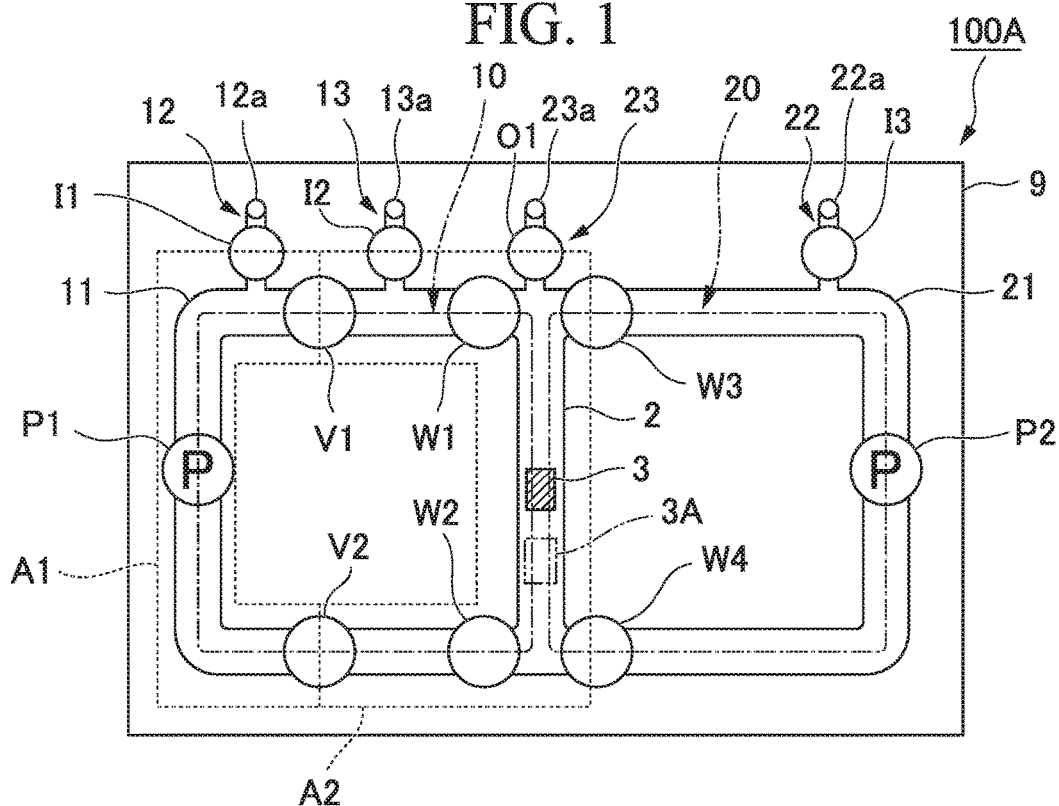
FIG. 1 is a plan view schematically showing a fluidic device according to a first embodiment.

Hereinafter, a fluidic device according to each embodiment will be described with reference to the drawings.

In the drawings used in the following description, characteristic portions may be enlarged for convenience in order to facilitate understanding of the features, and a dimensional ratio of each element may not be necessarily the same as an actual one.

First Embodiment

FIG. 1 is a plan view schematically showing a fluidic device 100A according to a first embodiment.

The fluidic device 100A of the embodiment is a device which detects a sample material to be detected contained in a specimen sample using a specific reaction such as an immune reaction (antigen-antibody reaction) and nucleic acid hybridization. The sample material is, for example, a biomolecule such as a nucleic acid, DNA, RNA, a peptide, a protein, an extracellular vesicle, and so on. The fluidic device 100A is constituted with a substrate board 9 in which flow paths and valves are formed.

The fluidic device 100A includes a first circulation flow path 10 and a second circulation flow path 20 which are formed in the substrate board 9 and circulate a solution containing a sample material. The first circulation flow path 10 and the second circulation flow path 20 share at least a part of the flow paths. That is, the first circulation flow path 10 and the second circulation flow path 20 have a shared flow path 2 which is shared with each other. Further, the first circulation flow path 10 has a non-shared flow path 11 which is not shared with the second circulation flow path 20.

Similarly, the second circulation flow path 20 has a non-shared flow path 21 which is not shared with the first circulation flow path 10.

(Shared Flow Path)

The shared flow path 2 connects ends of the non-shared flow path 11 of the first circulation flow path 10 to each other. Also, the shared flow path 2 connects ends of the non-shared flow path 21 of the second circulation flow path 20 to each other. The fluidic device 100A has a detection unit 3 in the shared flow path 2. A discharge flow path 23 is connected to one end of the shared flow path 2.

The detection unit 3 is provided to detect a sample material. The term "detecting a sample material" includes indirectly detecting a sample material. As an example in which a sample material is indirectly detected, the sample material may be bound to a detection auxiliary material which assists the detection of the sample material. When a labeling material (detection auxiliary material) is used, the sample material is bound to the detection auxiliary material by circulating and mixing in the first circulation flow path 10 together with the labeling material.

The detection unit 3 may be one for optically detecting the sample material, and may have, for example, an objective lens and an imaging unit. The imaging unit may have, for example, an electron-multiplying charge-coupled device (EMCCD) camera.

Also, the detection unit 3 may electrochemically detect the sample material and may have an electrode as an example.

Examples of the labeling material (detection auxiliary material) may include fluorescent dyes, fluorescent beads, fluorescent proteins, quantum dots, gold nanoparticles, biotin, antibodies, antigens, energy absorbing materials, radioactive isotopes, chemical luminescent bodies, enzymes and so on.

Examples of the fluorescent dyes include carboxyfluorescein (FAM), 6-carboxy-4', 5'-dichloro 2', 7'-dimethoxyfluorescein (JOE), fluorescein isothiocyanate (FITC), tetrachlorofluorescein (TET), 5'-hexachloro-fluorescein-CE phosphoramidite (HEX), Cy3, Cy5, Alexa 568, Alexa 647 and so on.

Examples of the enzymes include alkaline phosphatase, peroxidase and so on.

The detection unit 3 can detect the sample material by detecting the labeling material. When an enzyme is used as the labeling material, the sample material can be detected by detecting a reaction product such as a dye or fluorescence generated by a reaction with a substrate by the detection unit 3.

The detection unit 3 may be provided together with a capture unit 4 (described below with reference to FIG. 2) capable of capturing the sample material. The sample material captured by the capture unit 4 can be detected efficiently by disposing the detection unit 3 toward the capture unit 4 (refer to FIG. 2).

An outlet 23a for discharging a liquid is provided at an end of the discharge flow path 23. Also, a valve O1 is provided in the discharge flow path 23. In the fluidic device 100A, a liquid in the first circulation flow path 10 can be discharged by operating the opening and closing of the valve O1.

(First Circulation Flow Path)

The first circulation flow path 10 has metering valves V1 and V2, non-shared flow path end valves (valves) W1 and W2, and a pump P1 in the non-shared flow path 11. A first introduction flow path 12 and a second introduction flow path 13 are connected to the non-shared flow path 11 of the first circulation flow path 10.

The metering valves V1 and V2 are disposed so that each section of the first circulation flow path 10 partitioned by the metering valves has a predetermined volume. The metering valves V1 and V2 partition the first circulation flow path 10 into a first constant-quantity section A1 and a second constant-quantity section A2.

The non-shared flow path end valves W1 and W2 partition the first circulation flow path 10 into the shared flow path 2 and the non-shared flow path 11. The non-shared flow path end valves W1 and W2 are located at ends of the non-shared flow path 11. That is, the non-shared flow path end valves W1 and W2 are located in a flow path (the non-shared flow path 11) which is not shared by the first circulation flow path 10 in the vicinity of both ends of a flow path (the shared flow path 2) which is shared by the first circulation flow path 10. Both of the non-shared flow path end valves W1 and W2 are located in the second constant-quantity section A2. Therefore, an entire region of the shared flow path 2 is included in the second constant-quantity section A2 of the first circulation flow path 10.

The first introduction flow path 12 and the second introduction flow path 13 are connected to the non-shared flow path 11 of the first circulation flow path 10. The first introduction flow path 12 is connected to the first constant-quantity section A1, and the second introduction flow path 13 is connected to the second constant-quantity section A2. Further, an air flow path (not shown) for discharging or introducing air may be provided in the first constant-quantity section A1 and the second constant-quantity section A2. A discharge flow path for discharging the liquid may be further provided in the first constant-quantity section A1 and the second constant-quantity section A2. The introduction flow path or the discharge flow path of the liquid can also be used as the air flow path.

A liquid introduction inlet 12a is provided at an end of the first introduction flow path 12. A liquid introduction inlet 13a is provided at an end of the second introduction flow path 13. Also, a valve I1 is provided in the first introduction flow path 12. A valve I2 is provided in the second introduction flow path 13. In the fluidic device 100A, the first circulation flow path 10 may be filled with the liquid by operating the opening and closing of the valves I1 and I2.

One or both of the first introduction flow path 12 and the second introduction flow path 13 may be a discharge flow path for discharging the liquid from the first circulation flow path 10. In this case, in the fluidic device 100A, the discharge of the liquid and the air in the first circulation flow path 10 can be controlled by operating the opening and closing of the valves I1 and I2.

The first introduction flow path 12 can quantify an amount of liquid according to volumes of the first constant-quantity section A1 and the second constant-quantity section A2 by introducing the liquid to the first constant-quantity section A1. Similarly, the second introduction flow path 13 can quantify an amount of liquid according to a volume of the second constant-quantity section A2 by introducing the liquid into the second constant-quantity section A2.

The first introduction flow path 12 is disposed in the vicinity of the metering valve V1. When the liquid is introduced from the first introduction flow path 12 in a state in which the first constant-quantity section A1 is empty (in a state in which it is filled with air), air in the flow path is pushed out by the liquid, and the air is discharged from the air flow path (not shown). At this time, when the metering valve V1 and the first introduction flow path 12 are separated from each other, the air between the metering valve V1 and the first introduction flow path 12 is not discharged, an air pocket tends to be generated, and the liquid may not fill up to the metering valve V1. The generation of the air pocket can be minimized by disposing the first introduction flow path 12 and the second introduction flow path 13 in the vicinity of the metering valve V1, and it is possible to fill the first constant-quantity section A1 with an amount of liquid which is equal to the volume of the first constant-quantity section A1 and thus to realize accurate quantification. It is possible to realize accurate quantification within the second constant-quantity section A2 by disposing the second introduction flow path 13 in the vicinity of the metering valve V1 by the same action.

Even when the first introduction flow path 12 and the second introduction flow path 13 are used as the discharge flow paths for discharging the liquid, it is possible to minimize remaining liquid at the time of discharge by disposing them in the vicinity of the metering valve V2.

A pump P1 feeds and circulates the liquid in the first circulation flow path 10. The liquid circulating in the first circulation flow path 10 has a slow flow velocity around a wall surface and a high flow velocity in a center of the flow path due to an interaction (friction) between the flow path wall surface in the flow path and the solution. As a result, since distribution in the flow velocity of the liquid occurs, mixing of the solution is promoted. That is, convection occurs in the liquid in the first circulation flow path 10 by driving the pump P1, and the mixing of a plurality of liquids is promoted. The pump P1 may be a pump valve capable of feeding the liquid by opening and closing the valve.

(Second Circulation Flow Path)

The second circulation flow path 20 has non-shared flow path end valves (valves) W3 and W4 and a pump P2 in the non-shared flow path 21. A third introduction flow path 22 is connected to the non-shared flow path 21 of the second circulation flow path 20.

The non-shared flow path end valves W3 and W4 partition the second circulation flow path 20 into the shared flow path 2 and the non-shared flow path 21. The non-shared flow path end valves W3 and W4 are located at ends of the non-shared flow path 21. That is, the non-shared flow path end valves W3 and W4 are located in a flow path (the non-shared flow path 21) which is not shared by the second circulation flow path 20 in the vicinity of both ends of a flow path (the shared flow path 2) which is shared by the second circulation flow path 20.

The third introduction flow path 22 is connected to the non-shared flow path 21 of the second circulation flow path 20. Similarly to the first introduction flow path 12 and the second introduction flow path 13, a liquid introduction inlet 22a and a valve I3 are provided at an end of the third introduction flow path 22. In the fluidic device 100A, the second circulation flow path 20 may be filled with the liquid by operating the opening and closing of the valve I3. The third introduction flow path 22 can quantify the amount of liquid according to a volume of the second circulation flow path 20 by introducing the liquid into the second circulation flow path 20. Further, the third introduction flow path 22 may be a discharge flow path for discharging the liquid from the second circulation flow path 20. In the second circulation flow path, a discharge flow path for discharging the liquid may be provided separately from the third introduction flow path.

Also, an air flow path (not shown) for discharging or introducing air may be provided in the second circulation flow path 20. The introduction flow path or the discharge flow path of the liquid can also be used as the air flow path.

The pump P2 circulates the liquid in the second circulation flow path 20. Convection occurs in the liquid in the second circulation flow path 20 by driving the pump P2, and mixing of a plurality of liquids is promoted.

(Detection Method)

Next, a method of detecting a sample material using the fluidic device 100A of the embodiment will be described.

First, the metering valves V1 and V2 of the first circulation flow path 10 are closed, the non-shared flow path end valves W1 and W2 of the first circulation flow path 10 are opened, and the non-shared flow path end valves W3 and W4 of the second circulation flow path 20 are closed. Therefore, the first circulation flow path 10 is partitioned into the first constant-quantity section A1 and the second constant-quantity section A2. In this state, the specimen liquid containing the sample material is introduced from the first introduction flow path 12 into the first constant-quantity section A1 (specimen liquid introduction process). Further, a reagent liquid containing a labeling material (detection auxiliary material) is introduced from the second introduction flow path 13 into the second constant-quantity section A2 (reagent liquid introduction process). The specimen liquid and the reagent liquid can be quantified according to the volumes of the first constant-quantity section A1 and the second constant-quantity section A2 by the specimen liquid introduction process and the reagent liquid introduction process. The specimen liquid introduction process and the reagent liquid introduction process may be performed at the same time or may be performed in reverse order.

Then, the valves I1 and I2 are closed, and the metering valves V1 and V2 are opened. Therefore, the first circulation flow path 10 becomes a continuous loop. In this state, the specimen liquid and the reagent liquid are circulated and mixed in the first circulation flow path 10 by driving the pump P1 of the first circulation flow path 10 (first circulation process).

Then, in the second circulation flow path 20, a substrate liquid is introduced from the third introduction flow path 22 while the non-shared flow path end valves W3 and W4 are closed (substrate liquid introduction process). Therefore, the substrate liquid can be quantified according to the volume of the non-shared flow path 21 of the second circulation flow path 20. The substrate liquid is a liquid containing a substrate which produces a reaction product such as a dye or fluorescence by reaction with the labeling material.

Then, the non-shared flow path end valves W1 and W2 of the first circulation flow path 10 are closed, and the non-shared flow path end valves W3 and W4 of the second circulation flow path 20 are opened. Further, the substrate liquid and the mixed liquid of the specimen liquid and the reagent liquid in the shared flow path 2 are circulated and mixed in the second circulation flow path 20 (second circulation process). Therefore, the substrate contained in the substrate liquid reacts with the labeling material bound to the sample material. Subsequently, the reaction product (for example, dye or fluorescence) due to the reaction with the labeling material is detected by the detection unit, and thus the sample material is indirectly detected.

Through the above-described procedure, the sample material can be detected by the fluidic device 100A.

When the detection unit 3 is installed together with the capture unit 4 (refer to FIG. 2), the capture unit 4 may capture the sample material while the circulation is continued after the first circulation process in which the specimen liquid and the reagent liquid are mixed in the first circulation flow path 10, and the sample material may be separated from the mixed liquid of the specimen liquid and the reagent liquid by discharging the liquid from the first circulation flow path 10 via the discharge flow path 23 in a state in which the additional capturing is continued. Thereafter, impurities contained in the mixed liquid can be removed by filling the second circulation flow path 20 with the solution and circulating it, and a larger amount of the sample material than in a case in which the capture unit is not provided can be provided for the reaction in the second circulation flow path 20.

A flowing direction of the liquid in the shared flow path 2 in the first circulation process and a flowing direction of the liquid in the shared flow path in the second circulation process may be the same or opposite to each other. Further, the term "circulating" includes not only a case in which a fluid simply flows in one direction but also a case in which the fluid reciprocally flows in a circulation flow path at a constant cycle.

The fluidic device 100A of the embodiment has the first circulation flow path 10 and the second circulation flow path 20 which share the shared flow path 2. Therefore, at least some of the liquid circulated and mixed in the first circulation flow path 10 can be circulated in the second circulation flow path 20 without going through a transfer process. That is, it is possible to omit the transfer process, and thus it is possible to improve working efficiency and to enable detection in a short time. In addition, since a flow path for transferring between the first circulation flow path 10 and the second circulation flow path 20 is not required, a structure can be simplified, and an inexpensive fluidic device 100A can be provided.

Further, according to the fluidic device 100A of the embodiment, only some of the mixed liquid of the specimen liquid and the reagent liquid present in the shared flow path 2 circulates in the second circulation flow path 20. Impurities are often contained in the specimen liquid, and when the specimen liquid and the reagent liquid are mixed, foreign materials unnecessary for detection of the sample material may be generated in the mixed liquid in some cases. Such impurities and foreign materials may become background noise when the sample material is detected in the detection unit 3. Since only some of the mixed liquid is located in the second circulation flow path 20, the concentration of the background noise can be lowered in the second circulation flow path 20. Thus, detection accuracy of the sample material in the detection unit 3 can be improved.

Further, in the fluidic device 100A of the embodiment, the metering valves V1 and V2 are provided in the first circulation flow path 10. Therefore, it is possible to quantify the liquid in the first circulation flow path 10. Also, the first circulation flow path 10 becomes a continuous loop by opening the metering valves V1 and V2. Therefore, it is possible to efficiently perform mixing and to accelerate a reaction by circulating the quantified two liquids in the first circulation flow path 10.

Further, in the fluidic device 100A of the embodiment, the non-shared flow path end valves W1, W2, W3 and W4 are provided at the ends of the non-shared flow paths 11 and 12 of the first circulation flow path 10 and the second circulation flow path 20. Therefore, in the fluidic device 100A, it is possible to independently circulate a liquid (solution) in the first circulation flow path 10 and the second circulation flow path 20.

Further, in the fluidic device 100A of the embodiment, since the detection unit 3 is provided in the shared flow path 2, the circulating mixed liquid in the first circulation flow path 10 passes through the detection unit 3. Therefore, when the detection unit 3 is installed together with the capture unit 4 (refer to FIG. 2), capture efficiency of the capture unit 4 can be enhanced, and the detection accuracy in the detection unit 3 can be enhanced.

A plurality of detection units 3 and 3A may be provided in the shared flow path 2. In this case, the plurality of detection units 3 and 3A can detect different detection targets. Therefore, it is possible to simultaneously detect the specimen liquid containing a plurality of detection targets.

Second Embodiment

Figure 2:
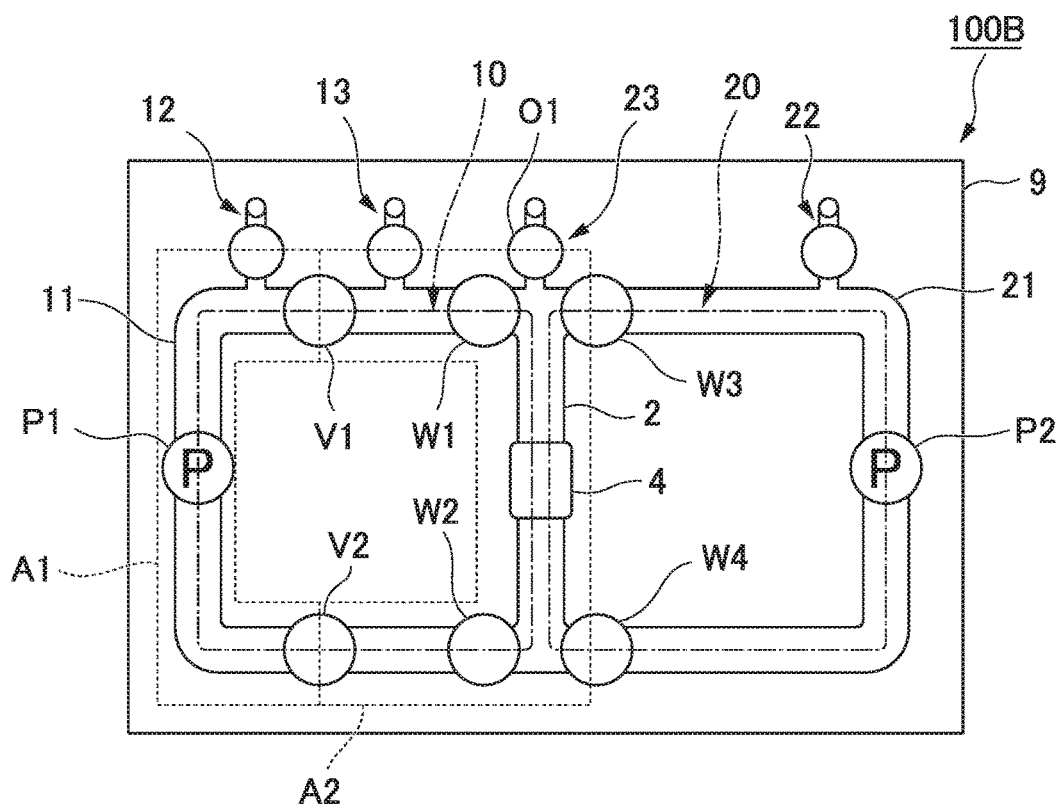
FIG. 2 is a plan view schematically showing a fluidic device according to a second embodiment.

FIG. 2 is a plan view schematically showing a fluidic device 100B according to a second embodiment. In FIG. 2, illustration of the air flow path for discharging the air in the flow path when the liquid is introduced is omitted.

The fluidic device 100B of the second embodiment is different from the first embodiment mainly in that the capture unit 4 instead of the detection unit 3 is provided in the shared flow path 2. The same reference numerals are given to the same elements as those in the above-described embodiment, and descriptions thereof will be omitted.

Like the first embodiment, the fluidic device 100B of the second embodiment includes the first circulation flow path 10 and the second circulation flow path 20 which circulate a solution containing a sample material. The first circulation flow path 10 and the second circulation flow path 20 have the shared flow path 2 which is shared with each other. The capture unit 4 is provided in shared flow path 2. The discharge flow path 23 is connected to one end of the shared flow path 2.

The capture unit 4 captures and collects the sample material in the solution circulating in the first circulation flow path 10.

Also, the capture unit 4 may capture carrier particles bound to the sample material. The capture unit 4 can collect the sample material from the liquid circulating in the first circulation flow path 10 by capturing the sample material itself or the carrier particles bound to the sample material. The fluidic device 100B can effectively concentrate, wash and transfer the sample material by having the capture unit 4.

The capture unit 4 of the embodiment is a unit which can capture the carrier particles by bringing a magnetic force generation source such as a magnet close to the capture unit 4, and the carrier particles are magnetic beads or magnetic particles. Other examples of the capture unit 4 include a column having a filler capable of being bound to the carrier particles, an electrode capable of attracting the carrier particles, and so on. Also, when the sample material is a nucleic acid, the capture unit 4 may be a nucleic acid array in which a nucleic acid hybridizing with this nucleic acid is immobilized.

As an example, the carrier particles are particles which can react with the sample material as a detection target. Examples of the reaction between the carrier particles and the sample material include, for example, a combination of the carrier particles and the sample material, adsorption between the carrier particles and the sample material, a modification of the carrier particles due to the sample material, a chemical change of the carrier particles due to the sample material, and so on.

Examples of the carrier particles include magnetic beads, magnetic particles, gold nanoparticles, agarose beads, plastic beads, and so on.

The carrier particles in which a material capable of being bound to or being adsorbed onto the sample material is provided on surfaces thereof may be used for the combination between the carrier particles and the sample material. For example, when the carrier particles and a protein are bound to each other, the protein can be bound to antibodies on the surfaces of the carrier particles using the carrier particles which have the antibodies capable of being bound to the protein on the surfaces thereof. The material capable of being bound to the sample material may be appropriately selected according to a type of the sample material. Examples of a combination of the material capable of being bound to or adsorbed onto the sample material/the sample material or a portion contained in the sample material include a biotin-binding protein such as avidin and streptavidin/biotin, an active ester group such as succinimidyl group/amino group, iodinated acetyl group/amino group, maleimide group/thiol group (—SH), maltose-binding protein/maltose, G protein/guanine nucleotide, polyhistidine peptide/metal ion such as nickel or cobalt, glutathione-S-transferase/glutathione, DNA-binding protein/DNA, antibody/antigen molecule (epitope), calmodulin/calmodulin-binding peptide, ATP-binding protein/ATP, various receptor proteins/ligands thereof such as estradiol receptor protein/estradiol, and so on.

The carrier particles and the sample material may react in the first circulation flow path 10. For example, a complex in which the carrier particles and the sample material are bound is formed by introducing a liquid containing the carrier particles and the sample material into the first circulation flow path 10 and rotationally mixing them in the circulation flow path. For example, when a biomolecule is fixed on the particle surface and a sample material which binds to the biomolecule on the particle surface is present in the liquid, it is possible to increase a collision frequency and to improve a binding reaction rate between them by mixing. This technique is suitable for, for example, immunoassay in which measurement of a single item is mainstream.

Preferably, a magnetic force of the capture unit 4 can be controllable. Capturing and releasing (non-capturing) of the carrier particles can be controlled by controlling a magnetic force of the magnetic force generation source which is applied to the carrier particles. That is, the capture unit 4 is constituted to be capable of controlling the affinity for carrier particles. For example, the capture unit 4 may control the magnetic force applied to the carrier particles by changing a distance between the magnet and the circulation flow path. As the carrier particles are released from a captured state, the carrier particles are again dispersed in the solution. When an electromagnet is used in the capture unit 4, the magnetic force may be controlled by ON/OFF of a current and control of a current value, and the capturing and releasing of the carrier particles by the capture unit 4 may be performed.

The capture unit 4 may be in the form of an array in which the carrier particles can be arranged. Examples of such a form include one in which regions capable of capturing the carrier particles are disposed in an array, one in which holes capable of receiving the carrier particles are disposed in an array, and so on. For example, the region capable of capturing the carrier particles may be in the form of a well, and a size of the well may be 1 to 2 times a diameter of the carrier particle so that one carrier particle is accommodated. Further, the capturing means may be a magnet array in which a plurality of magnets are arranged in an array. In the capture unit 4, the sample material bound to the carrier particles may be analyzed in a state in which the carrier particles are captured. The analysis of the sample material bound to the carrier particles becomes efficient by arranging and capturing the carrier particles.

(Purification Method)

Next, a method of purifying the sample material using the fluidic device 100B of the embodiment will be described.

First, the valves W3 and W4 are closed, the first circulation flow path 10 is partitioned into the first constant-quantity section A1 and the second constant-quantity section A2, a specimen liquid (a first liquid) containing a sample material is introduced from the first introduction flow path 12 into the first constant-quantity section A1 (specimen liquid introduction process), and a first reagent liquid (a second liquid) containing the carrier particles is introduced from the second introduction flow path 13 to the second constant-quantity section A2 (first reagent liquid introduction process).

Then, the valves I1 and I2 are closed, the metering valves V1 and V2 are opened, the specimen liquid and the reagent are circulated and mixed in the first circulation flow path 10 by driving the pump P1 of the first circulation flow path 10, and thus a mixed liquid is obtained (first circulation process). Therefore, the sample material in the specimen liquid and the carrier particles in the reagent react and bind to each other, and a complex of the carrier particles and the sample material is produced.

Next, in a state in which the mixed liquid is further circulated in the first circulation flow path 10, the complex of the sample material and the carrier particles is captured by the capture unit 4. After the binding between the sample material and the carrier particles has progressed sufficiently, the complex of the sample material and the carrier particles is captured in the capture unit 4. The capturing of the complex of the sample material and the carrier particles by the capture unit 4 may be preferably carried out in parallel with the first circulation process. An opportunity to be captured by the capture unit 4 is increased by circulating the liquid containing the complex of the sample material and the carrier particles, and the capturing of the complex of the sample material and the carrier particles can be performed with high efficiency.

Next, the mixed liquid is discharged from the first circulation flow path 10 via the discharge flow path 23 in a state in which the circulation of the mixed liquid in the first circulation flow path 10 and the capturing of the sample material in the capture unit 4 are continued. Therefore, the mixed liquid is removed in the shared flow path 2, and the complex of the sample material and the carrier particles is separated from the mixed liquid.

Next, the non-shared flow path end valves W1 and W2 and the valve O1 are closed and the non-shared flow path end valves W3 and W4 are opened so that the second circulation flow path 20 is formed as a continuous loop. Further, a second reagent liquid (a third solution) is introduced from the third introduction flow path 22 (second reagent liquid introduction process). The second reagent liquid of the embodiment is an eluate which elutes (releases) the sample material from the complex of the sample material and the carrier particles. In addition, the second reagent liquid may be a solution suitable for preservation of the sample material or a solution suitable for a next process using the sample material.

Then, the capturing in the capture unit 4 is canceled, and the pump P2 is driven to circulate the second reagent liquid (third liquid) and the complex of the sample material and the carrier particles in the second circulation flow path 20. Therefore, the sample material is released from the complex.

Then, in the capture unit 4, the carrier particles are captured. Thus, the carrier particles can be removed from the liquid. Further, the liquid containing the sample material is discharged and recovered from the discharge flow path 23 connected to the shared flow path 2.

In the embodiment, the case in which the capturing of the complex of the sample material and the carrier particles in the capture unit 4 is canceled and the second reagent liquid is circulated has been exemplified. However, the second reagent liquid may be circulated in a state in which the complex is captured in the capture unit 4. Therefore, since only the sample material is released into the second reagent liquid, the liquid containing the sample material can be discharged and recovered from the discharge flow path 23 connected to the shared flow path 2.

Furthermore, the complex of the sample material and the carrier particles which is captured in the capture unit 4 may be washed by introducing a washing liquid into the first circulation flow path 10 or the second circulation flow path 20 and circulating it before the introduction of the second reagent liquid.

The fluidic device 100B of the embodiment can achieve the same effect as the first embodiment by having the first circulation flow path 10 and the second circulation flow path 20 which have the shared flow path 2.

Further, the fluidic device 100B of the embodiment has the capture unit 4 in the shared flow path 2. Therefore, it is possible to concentrate and move a product from the first circulation flow path 10 to the second circulation flow path 20 by opening the second circulation flow path 20 after the product (the sample material to which the carrier particles are bound) of the two liquids mixed in the first circulation flow path 10 is captured in the capture unit 4. Furthermore, according to the embodiment, when the washing liquid is introduced into the second circulation flow path 20, it can be easily washed.

Third Embodiment

Figure 3:
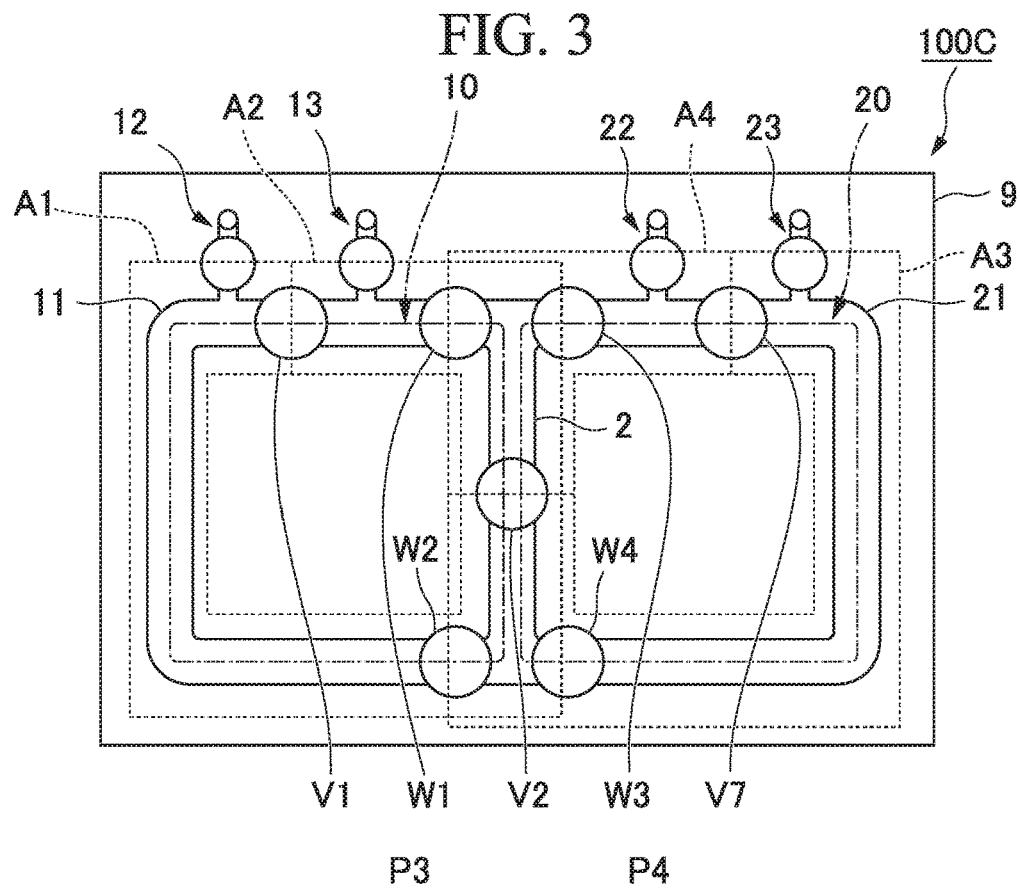
FIG. 3 is a plan view schematically showing a fluidic device according to a third embodiment.

FIG. 3 is a plan view schematically showing a fluidic device 100C according to a third embodiment. In FIG. 3, illustration of the air flow path for discharging the air in the flow path when the liquid is introduced is omitted.

The fluidic device 100C of the third embodiment is different from the first embodiment mainly in the constitution of the metering valve V2. The same reference numerals are given to the same elements as those in the above-described embodiment, and descriptions thereof will be omitted.

Like the first embodiment, the fluidic device 100C of the third embodiment includes the first circulation flow path 10 and the second circulation flow path 20 which circulate a solution containing a sample material. The first circulation flow path 10 and the second circulation flow path 20 have the shared flow path 2 which is shared with each other.

The first circulation flow path 10 of the fluidic device 100C has the metering valve V1 in the non-shared flow path 11 and the metering valve V2 in the shared flow path. Also, the first circulation flow path 10 has the non-shared flow path end valves (valves) W1 and W2. The metering valves V1 and V2 partition the first circulation flow path 10 into the first constant-quantity section A1 and the second constant-quantity section A2. Since the metering valve V2 is located in the shared flow path 2, the first constant-quantity section A1 and the second constant-quantity section A2 are disposed over the shared flow path 2 and the non-shared flow path 11. Also, the first introduction flow path 12 is connected to the first constant-quantity section A1, and the second introduction flow path 13 is connected to the second constant-quantity section A2.

In the first circulation flow path 10, the metering valve V1, the non-shared flow path end valve W1 and the metering valve V2 are arranged in this order to constitute a pump P3. The pump P3 can transfer the liquid in the circulation flow path by sequentially opening and closing the three valves (pump valves) V1, W1 and V2. That is, in the embodiment, the metering valve also serves as a pump valve. Thus, it is possible to provide the fluidic device 100C having a simple structure by reducing the number of valves.

The second circulation flow path 20 of the fluidic device 100C has a metering valve V7 in the non-shared flow path 21 and the metering valve V2 in the shared flow path. Further, the second circulation flow path 20 has the non-shared flow path end valves (valves) W3 and W4. The metering valves V7 and V2 partition the second circulation flow path 20 into a third constant-quantity section A3 and a fourth constant-quantity section A4. Since the metering valve V2 is located in the shared flow path 2, the third constant-quantity section A3 and the fourth constant-quantity section A4 are disposed over the shared flow path 2 and the non-shared flow path 11. Also, the first introduction flow path 12 is connected to the first constant-quantity section A1, and the second introduction flow path 13 is connected to the second constant-quantity section A2.

In the second circulation flow path 20, the metering valve V7, the non-shared flow path end valve W3 and the metering valve V2 are arranged in this order to constitute the pump P4.

In this way, when the valve is disposed in the shared flow path, since it can be used as the metering valve and/or the pump valve in both the first circulation flow path 10 and the second circulation flow path 20, the constitution of the fluidic device can be simplified.

As described in the embodiment, as the metering valve V2 is provided in the shared flow path 2, the fluidic device 100C can form various partitioned regions by opening and closing the respective valves and can perform a variety of quantitative determinations.

The fluidic device 100C of the embodiment has the same effects as those in the first embodiment by having the first circulation flow path 10 and the second circulation flow path 20 which have the shared flow path 2.

Fourth Embodiment

Figure 4:
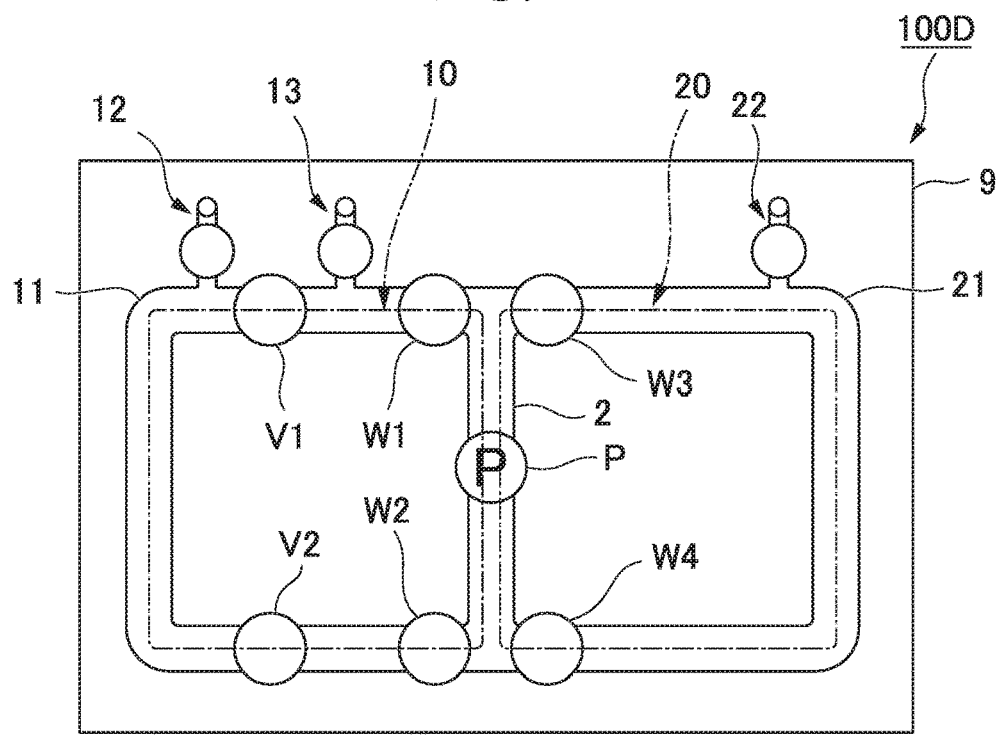
FIG. 4 is a plan view schematically showing a fluidic device according to a fourth embodiment.

FIG. 4 is a plan view schematically showing a fluidic device 100D according to a fourth embodiment. In FIG. 4, illustration of the air flow path for discharging the air in the flow path when the liquid is introduced is omitted.

The fluidic device 100D of the fourth embodiment is different from the first embodiment mainly in that a pump P is provided in the shared flow path 2. The same reference numerals are given to the same elements as those in the above-described embodiment, and descriptions thereof will be omitted.

Like the first embodiment, the fluidic device 100D of the fourth embodiment includes the first circulation flow path 10 and the second circulation flow path 20 which circulate a solution containing a sample material. The first circulation flow path 10 and the second circulation flow path 20 have the shared flow path 2 which is shared with each other. The fluidic device 100D has a pump P in the shared flow path 2, and the pump is not provided in the non-shared flow paths 11 and 21 of the first circulation flow path 10 and the second circulation flow path 20.

According to the fluidic device 100D of the embodiment, circulation of the liquid in each of the first circulation flow path 10 and the second circulation flow path 20 can be performed by driving of one pump P. According to the embodiment, it is possible to provide the fluidic device 100D inexpensively by reducing the number of pumps mounted in the fluidic device 100D.

Fifth Embodiment

Figure 5:
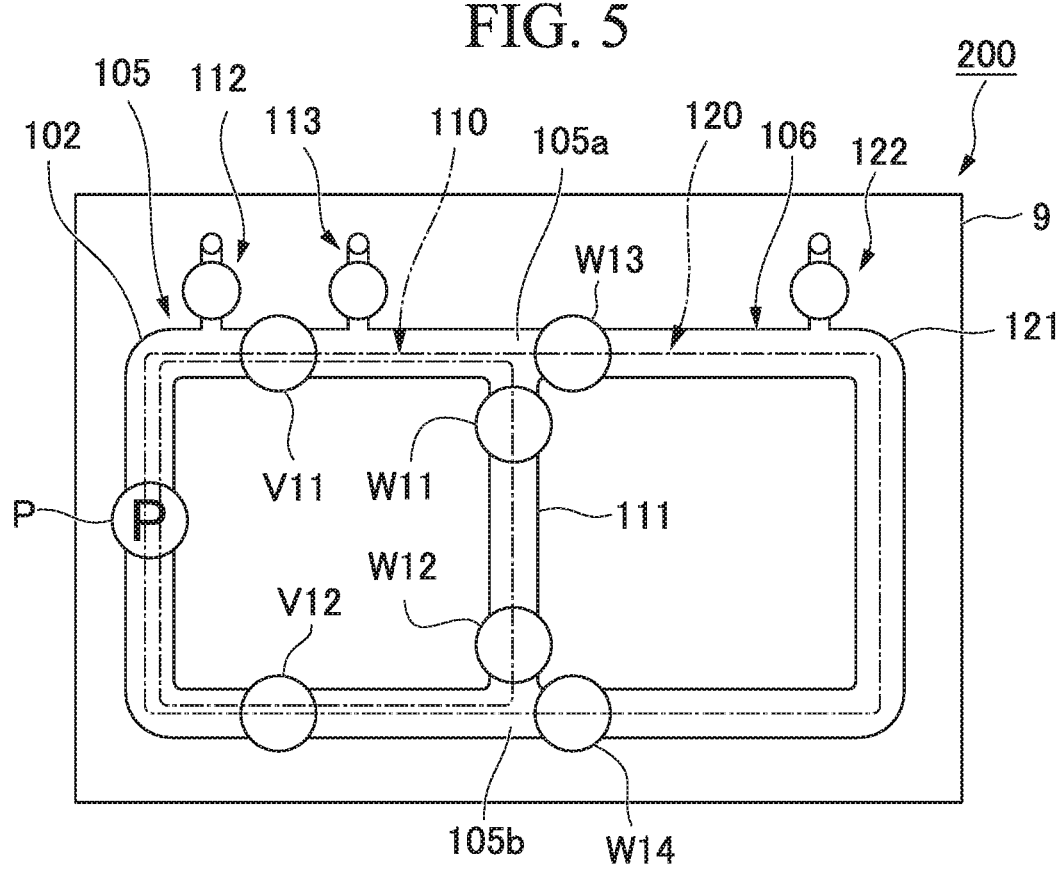
FIG. 5 is a plan view schematically showing a fluidic device according to a fifth embodiment.

FIG. 5 is a plan view schematically showing a fluidic device 200 according to a fifth embodiment. In FIG. 5, illustration of the air flow path for discharging the air in the flow path when the liquid is introduced is omitted. In the description of the embodiment, the same reference numerals are given to the same elements as those in the above-described embodiment, and descriptions thereof will be omitted.

The fluidic device 200 of the fifth embodiment includes a loop flow path 105 and a bypass flow path 106.

The loop flow path 105 is an annular flow path located on the left side of FIG. 5 and constitutes a first circulation flow path 110. A first connecting portion 105a and a second connecting portion 105b to which the bypass flow path 106 is connected are provided in a flow path of the loop flow path 105. The first connecting portion 105a and the second connecting portion 105b are branching portions which branch in three directions in the form of a three-way path.

As described above, the loop flow path 105 includes the annular first circulation flow path 110 and a part of a second circulation flow path 120 which will be described below. Therefore, the flow paths constituting the loop flow path 105 are classified into a shared flow path 102 which is shared by the first circulation flow path 110 and the second circulation flow path 120 and a non-shared flow path 111 which is a part of the first circulation flow path 110 and does not constitute the second circulation flow path 120. The second circulation flow path 120 has a non-shared flow path 121.

The shared flow path 102 of the loop flow path 105 has metering valves V11 and V12 and a pump P. In addition, a first introduction flow path 112 and a second introduction flow path 113 are connected to the shared flow path 102.

Non-shared flow path end valves W11 and W12 are provided at ends of the non-shared flow path 111 of the loop flow path 105.

The bypass flow path 106 is formed to detour by connecting the first connecting portion 105a to the second connecting portion 105b. Non-shared flow path end valves W13 and W14 are provided at both ends of the bypass flow path 106. In addition, a third introduction flow path 122 is connected to the bypass flow path 106.

The bypass flow path 106 and the shared flow path 102 of the loop flow path 105 constitute the second circulation flow path 120. The second circulation flow path 120 is constituted by the bypass flow path 106 and one of the two flow paths partitioned by the first connecting portion 105a and the second connecting portion 105b which is a part of the loop flow path 105 and has a long distance.

According to the embodiment, the pump P is provided in the shared flow path 102 of the first circulation flow path 110 and the second circulation flow path 120. Therefore, circulation of the liquid in each of the first circulation flow path 110 and the second circulation flow path 120 can be performed by driving of one pump P. Further, according to the embodiment, since the two metering valves V11 and V12 are provided in the shared flow path 102, various partitioned regions can be formed in the first circulation flow path 110 and the second circulation flow path 120 by opening and closing the respective valves, and a variety of quantitative determinations can be performed.

Sixth Embodiment

Figure 6:
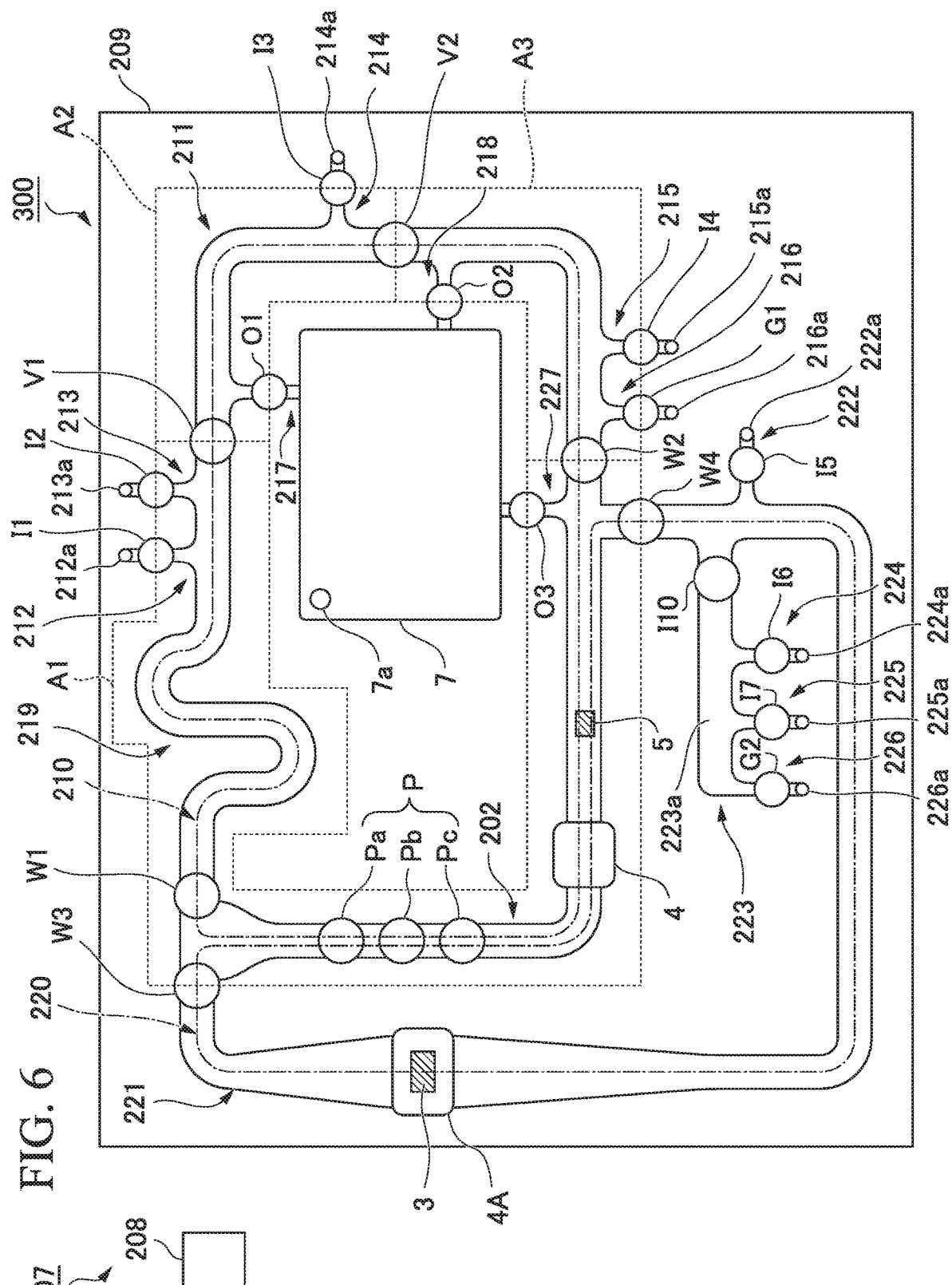
FIG. 6 is a plan view schematically showing a fluidic device according to a sixth embodiment.

FIG. 6 is a plan view schematically showing a fluidic device 300 according to a sixth embodiment. In the description of the embodiment, the same reference numerals are given to the same elements as those in the above-described embodiment, and descriptions thereof will be omitted.

The fluidic device 300 comprises a substrate board 209 in which flow paths and valves are formed. The fluidic device 300 includes a first circulation flow path 210 and a second circulation flow path 220 which are formed in the substrate board 209 and circulate a solution containing a sample material. The first circulation flow path 210 and the second circulation flow path 220 have a shared flow path 202 which is shared with each other. Further, the first circulation flow path 210 has a non-shared flow path 211 which is not shared with the second circulation flow path 220. The second circulation flow path 220 has a non-shared flow path 221 which is not shared with the first circulation flow path 210.

(Shared Flow Path)

The shared flow path 202 connects ends of the non-shared flow path 211 of the first circulation flow path 210 to each other. Further, the shared flow path 202 connects ends of the non-shared flow path 221 of the second circulation flow path 220. The shared flow path 202 has a pump P, a first capture unit (capture unit) 4, and an auxiliary material detection unit 5.

A discharge flow path 227 connected to a waste liquid tank 7 is connected to the shared flow path 202. A discharge flow path valve O3 is provided in the discharge flow path 227.

The pump P is constituted by three pump valves Pa, Pb and Pc disposed side by side in the flow path. The pump P can control a transferring direction of the solution in the circulation flow paths by controlling the opening and closing of the three pump valves Pa, Pb and Pc. The number of valves constituting the pump valve may be 4 or more.

The auxiliary material detection unit 5 is provided to detect a labeling material (detection auxiliary material) which is bound to the sample material and assists the detection of the sample material. When an enzyme is used as the labeling material, degradation of the enzyme may occur as a storage time becomes longer, and detection efficiency in the detection unit 3 provided in the second circulation flow path 220 may be lowered. The auxiliary material detection unit 5 detects the labeling material and measures a degree of degradation of the enzyme.

(First Circulation Flow Path)

The first circulation flow path 210 has a plurality of valves V1, V2, W1 and W2 in the non-shared flow path 211. Among these valves, the valves V1, V2 and W2 serve as metering valves. In addition, the valves W1 and W2 serve as non-shared flow path end valves. That is, the valve W2 serves not only as a metering valve but also as a non-shared flow path end valve.

The metering valves V1, V2 and W2 are disposed so that each of sections of the first circulation flow path 210 partitioned by the metering valves has a predetermined volume. The metering valves V1 and V2 partition the first circulation flow path 210 into a first constant-quantity section A1, a second constant-quantity section A2, and a third constant-quantity section A3.

The first constant-quantity section A1 includes the shared flow path 202.

Introduction flow paths 212 and 213 are connected to the non-shared flow path 211 of the first constant-quantity section A1. An introduction flow path 214 and a discharge flow path 217 are connected to the second constant-quantity section A2. An introduction flow path 215, a discharge flow path 218 and an air flow path 216 are connected to the third constant-quantity section A3.

The introduction flow paths 212, 213, 214 and 215 are provided to introduce different liquids into the first circulation flow path 210. An introduction flow path valve I1 for opening and closing the introduction flow path is provided in the introduction flow path 212. An introduction flow path valve I2 for opening and closing the introduction flow path is provided in the introduction flow path 213. An introduction flow path valve I3 for opening and closing the introduction flow path is provided in the introduction flow path 214. An introduction flow path valve I4 for opening and closing the introduction flow path is provided in the introduction flow path 215. Further, a liquid introduction inlet 212a which opens on a surface of the substrate board 209 is provided at an end of the introduction flow path 212. A liquid introduction inlet 213a which opens on the surface of the substrate board 209 is provided at an end of the introduction flow path 213. A liquid introduction inlet 214a which opens on the surface of the substrate board 209 is provided at an end of the introduction flow path 214. A liquid introduction inlet 215a which opens on the surface of the substrate board 209 is provided at an end of the introduction flow path 215.

The air flow path 216 is provided to discharge air or introduce air from the first circulation flow path 210. An air flow path valve G1 for opening and closing a flow path is provided in the air flow path 216.

An air introduction inlet 216a which opens on the surface of the substrate board 209 is provided at an end of the air flow path 216.

The discharge flow paths 217 and 218 are provided to discharge the liquid from the first circulation flow path 210. A discharge flow path valve O1 for opening and closing the discharge flow path is provided in the discharge flow path 217. A discharge flow path valve O2 for opening and closing the discharge flow path is provided in the discharge flow path 218. The discharge flow paths 217 and 218 are connected to the waste liquid tank 7. An outlet 7a which is connected to an external suction pump (not shown) and which opens on the surface of the substrate board for negative pressure suction is provided in the waste liquid tank 7. In the fluidic device 300 of the embodiment, the waste liquid tank 7 is disposed in an inner region of the first circulation flow path 210. Therefore, the fluidic device 300 can be miniaturized.

A meandering portion 219 is provided in the non-shared flow path 211 of the first constant-quantity section A1. The meandering portion 219 is a part of the non-shared flow path 211 of the first constant-quantity section A1 and is a portion formed to meander right and left. The meandering portion 219 increases the volume of the non-shared flow path 211 of the first constant-quantity section A1.

(Second Circulation Flow Path)

The second circulation flow path 220 has valves W3 and W4 serving as non-shared flow path end valves, a detection unit 3 and a second capture unit 4A in the non-shared flow path 221. The second capture unit 4A has the same structure as the above-described capture unit 4. The second capture unit 4A and the detection unit 3 are disposed to overlap each other.

An introduction flow path 222 and an aggregation flow path 223 are connected to the non-shared flow path 221 of the second circulation flow path 220. A liquid reservoir portion 223a and a valve I10 are provided in the aggregation flow path 223. The valve I10 is located between the liquid reservoir portion 223a and the second circulation flow path 220. Introduction flow paths 224 and 225 and an air flow path 226 are connected to the liquid reservoir portion 223a. An introduction flow path valve I5 is provided in the course of the introduction flow path 222. An introduction flow path valve I6 is provided in the course of the introduction flow path 224. An introduction flow path valve I7 is provided in the course of the introduction flow path 225. An introduction inlet 222a is provided at an end of the introduction flow path 222. An introduction inlet 224a is provided at an end of the introduction flow path 224. An introduction inlet 225a is provided at an end of the introduction flow path 225. Similarly, an air flow path valve G2 is provided in the course of the air flow path 226. An air introduction inlet 226a is provided at an end of the air flow path 226.

(Detection Method)

Next, a mixing method, a capture method and a detection method of a sample material using the fluidic device 300 according to the embodiment will be described. In the detection method of the embodiment, an antigen (sample material, biomolecule) to be detected contained in a specimen sample is detected by an immunological reaction and an enzymatic reaction.

First, the valves V1, V2 and W2 of the first circulation flow path 210 are closed, the valve W1 is opened, and the non-shared flow path end valves W3 and W4 of the second circulation flow path 220 are closed. Therefore, the first circulation flow path 210 is partitioned into the first constant-quantity section A1, the second constant-quantity section A2 and the third constant-quantity section A3.

Figure 7:
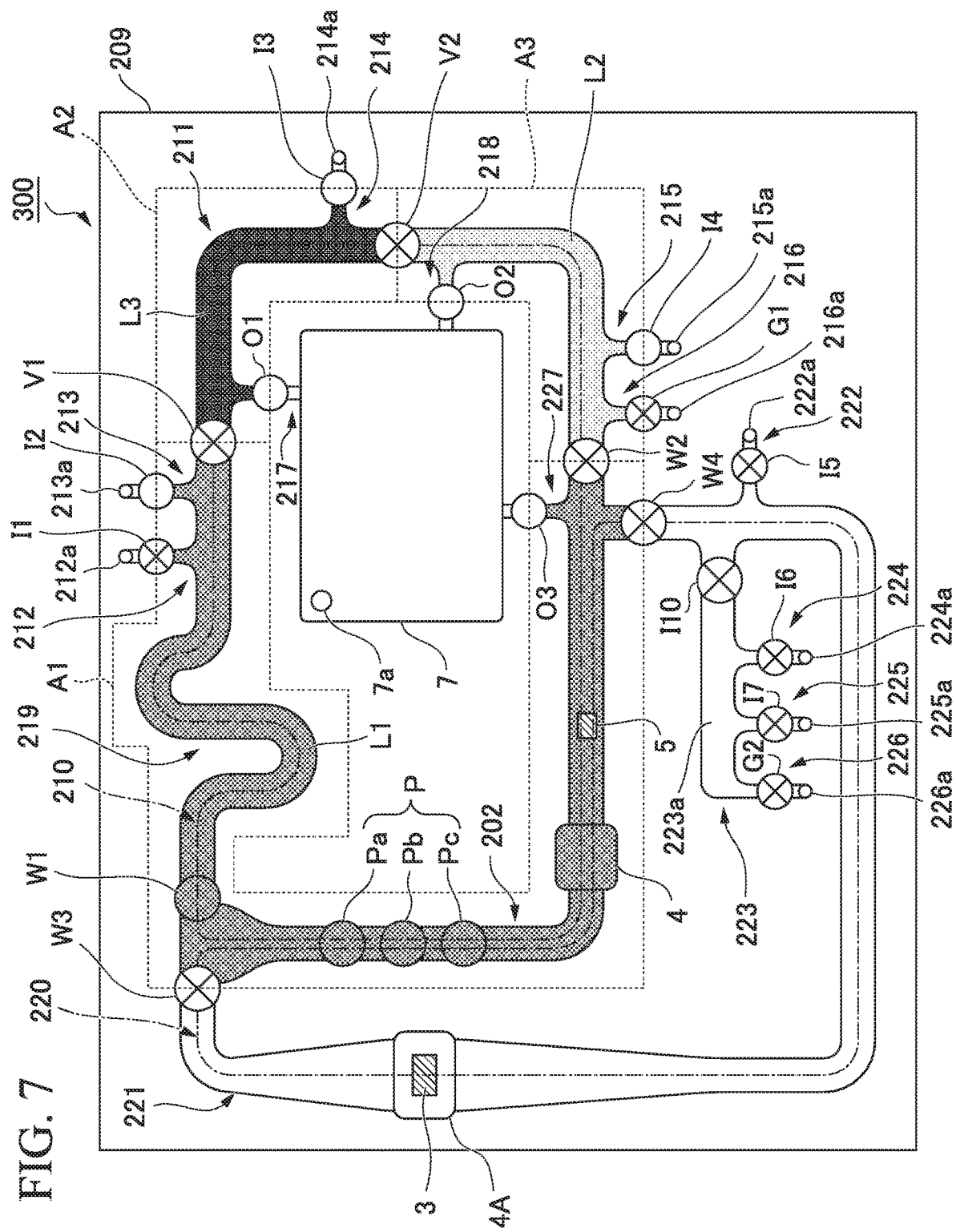
FIG. 7 is a view showing a process in which a specimen liquid, a first reagent liquid and a second reagent liquid are introduced into a first circulation flow path in a detection method using the fluidic device of the sixth embodiment.

Then, as shown in FIG. 7, a specimen liquid (first liquid) L1 containing a sample material is introduced from the introduction flow path 213 into the first constant-quantity section A1 (specimen liquid introduction process). Also, a second reagent liquid L3 containing a labeling material (detection auxiliary material) is introduced from the introduction flow path 214 into the second constant-quantity section A2 (second reagent liquid introduction process), and a first reagent liquid (second liquid) L2 containing carrier particles is introduced from the introduction flow path 215 into the third constant-quantity section A3 (first reagent liquid introduction process).

In the embodiment, the specimen liquid L1 includes an antigen as a detection target (sample material). Examples of the specimen liquid include body fluids such as blood, urine, saliva, plasma and serum, cell extracts, tissue disruption liquid, and so on.

Also, in the embodiment, magnetic particles are used as the carrier particles contained in the first reagent liquid L2. An antibody A which specifically binds to the antigen to be detected (sample material) is immobilized on the surfaces of the magnetic particles.

Further, in the embodiment, the second reagent liquid L3 contains an antibody B which specifically binds to the antigen to be detected. Alkaline phosphatase (detection auxiliary material, enzyme) is immobilized and labeled on the antibody B.

Figure 8:
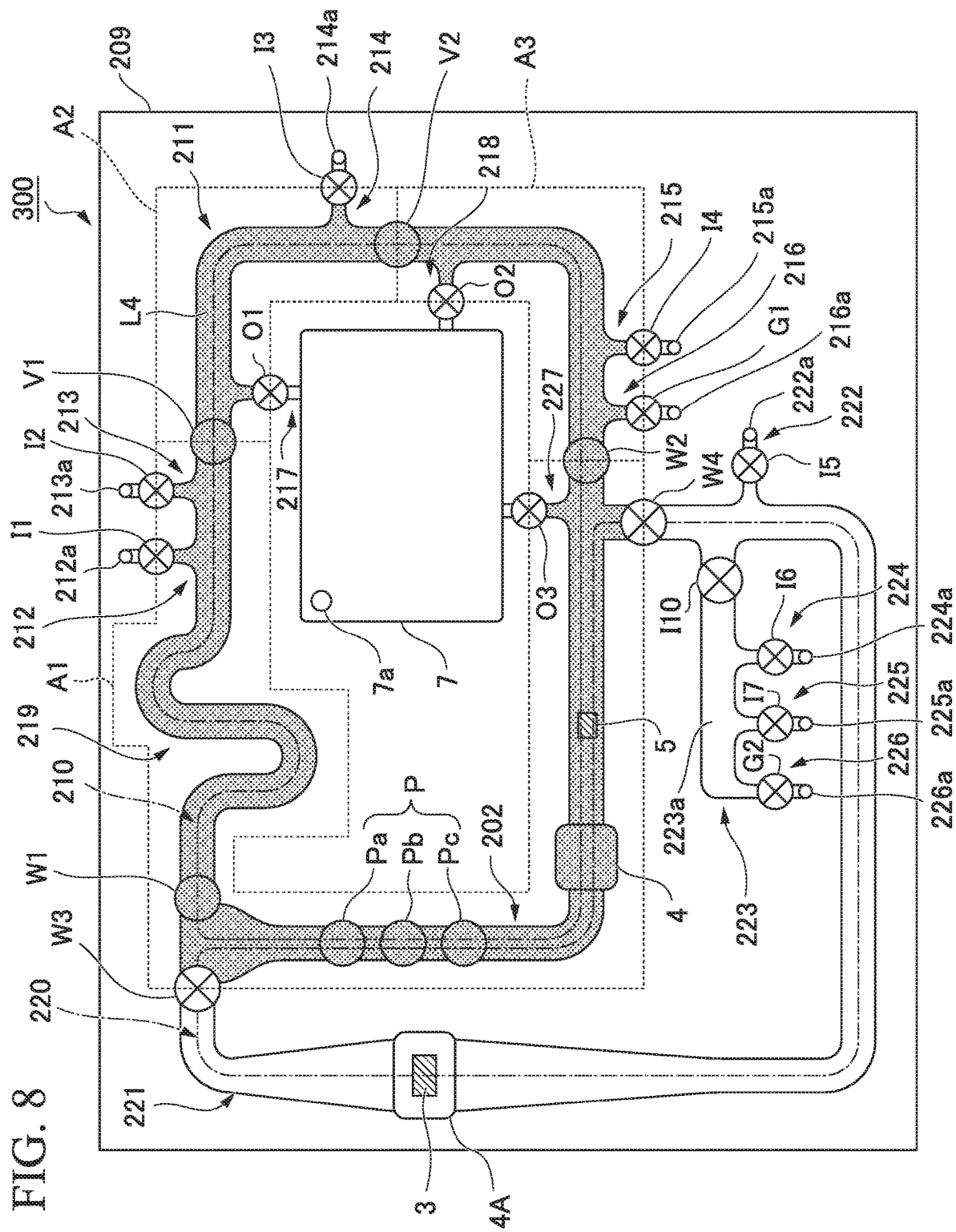
FIG. 8 is a view showing a process in which the specimen liquid, the first reagent liquid and the second reagent liquid are circulated and mixed in the first circulation flow path in the detection method using the fluidic device according to the sixth embodiment.

Then, as shown in FIG. 8, the specimen liquid L1, the first reagent liquid L2 and the second reagent liquid L3 are circulated and mixed in the first circulation flow path 210 by opening the valves V1, V2 and W2 and driving the pump P of the shared flow path 202, and thus a mixed liquid L4 is obtained (first circulation process). The antigen is bound to the antibody A immobilized on the carrier particles by mixing the specimen liquid L1, the first reagent liquid L2 and the second reagent liquid L3, and the antibody B to which the enzyme is immobilized is bound to the antigen. Therefore, a carrier particle-antigen-enzyme complex is produced in the mixed liquid L4.

In addition, in the first circulation process, an excess labeling material which does not form the carrier particle-antigen-enzyme complex is captured by the auxiliary material detection unit 5.

Furthermore, after the binding between the sample material and the carrier particles is sufficiently advanced, the magnet for capturing magnetic particles in the first capture unit 4 is brought close to the flow path in a state in which the mixed liquid LA is circulated in the first circulation flow path 210. Therefore, the first capture unit 4 captures the carrier particle-antigen-enzyme complex. The complex is captured on an inner wall surface of the first circulation flow path 210 in the first capture unit 4 and separated from the liquid component.

Then, although illustration of the process is omitted, while the carrier particle-antigen-enzyme complex is captured in the first capture unit 4, the air flow path valve G1 and the discharge flow path valves O1, O2 and O3 are opened so that the negative pressure suction from the outlet 7a of the waste liquid tank 7 is performed and the liquid component is discharged (mixed liquid discharge process). Therefore, in the shared flow path 202, the mixed liquid is removed, and the carrier particle-antigen-enzyme complex is separated from the mixed liquid.

Then, although illustration of the process is omitted, the air flow path valve G1 and the discharge flow path valves O1, O2 and O3 are closed, and the washing liquid is introduced from the introduction flow path 212 into the first circulation flow path 210. Also, the washing liquid is circulated in the first circulation flow path 210 by driving the pump P of the shared flow path 202, and the carrier particle-antigen-enzyme complex is washed. Furthermore, after the circulation of the washing liquid for a certain period of time is completed, the washing liquid is discharged to the waste liquid tank 7.

A cycle of introduction, circulation and discharge of the washing liquid may be performed a plurality of times. Removal efficiency of unnecessary materials can be enhanced by repeatedly performing the introduction, circulation and discharge of the washing liquid.

Figure 9:
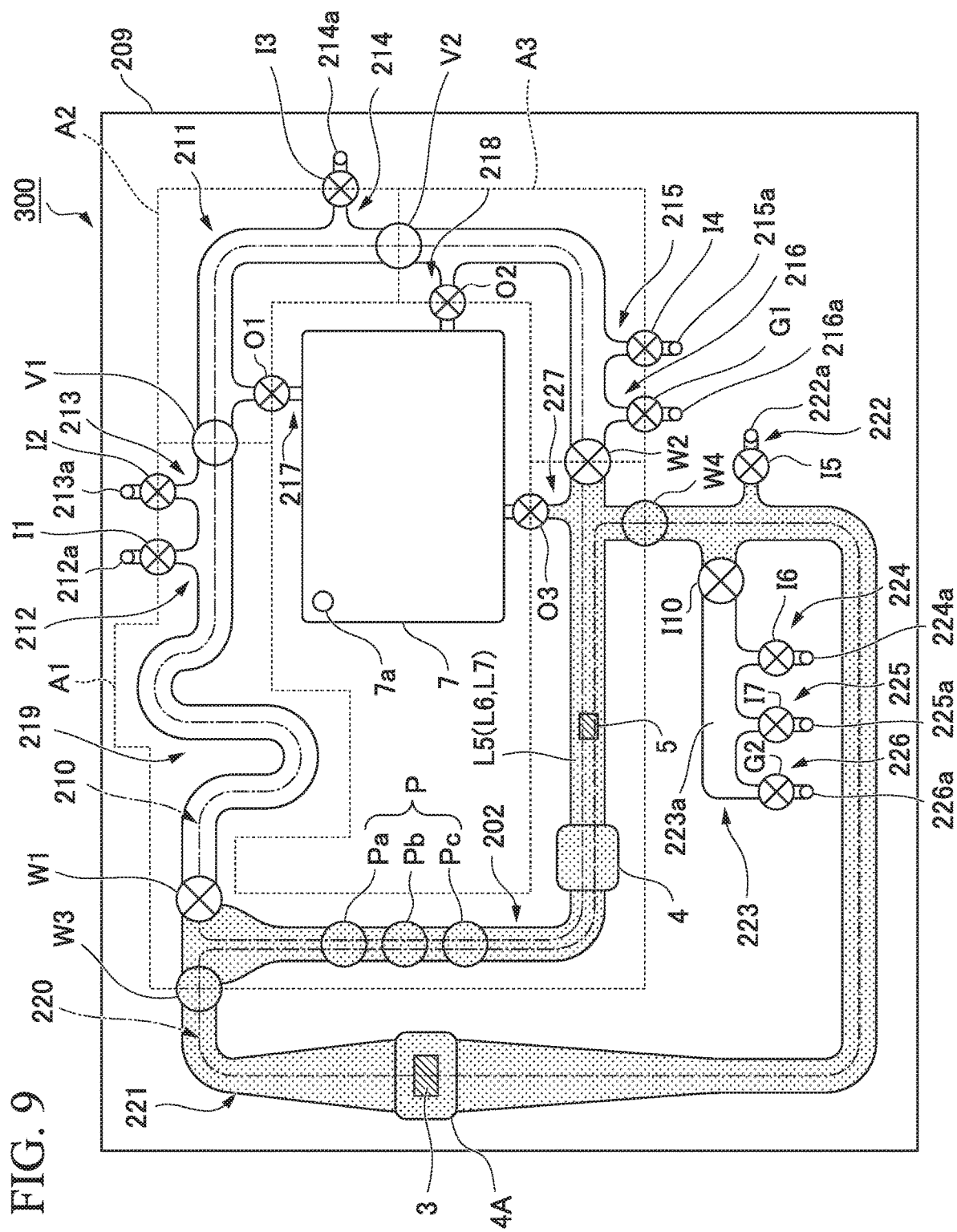
FIG. 9 is a view showing a process in which a transfer liquid, a substrate liquid or a measurement liquid is circulated in a second circulation flow path in the detection method using the fluidic device according to the sixth embodiment.

Then, as shown in FIG. 9, the valves W1 and W2 of the first circulation flow path 210 are closed, the non-shared flow path end valves W3 and W4 of the second circulation flow path 220 are opened, a transfer liquid L5 is introduced from the introduction flow path 222, and the second circulation flow path 220 is filled with the transfer liquid L5. Next, the capturing of the carrier particle-antigen-enzyme complex in the first capture unit 4 is canceled, and the carrier particle-antigen-enzyme complex is transferred to the second circulation flow path 220 by driving the pump P. Further, in a state in which the pump P is driven, the magnet which captures the magnetic particles is brought close to the flow path in the second capture unit 4A, and the carrier particle-antigen-enzyme complex is captured. Therefore, the carrier particle-antigen-enzyme complex is captured on the inner wall surface of the second capture unit 4A and separated from the liquid component. It is possible to perform the detection with a clean flow path without contamination due to the specimen liquid or the like by moving the carrier particle-antigen-enzyme complex from the capture unit 4 to the capture unit 4A.

Then, the valve W4 is closed, the air flow path valve G2 of the air flow path 226 and the discharge flow path valve O3 of the discharge flow path 227 are opened, and the negative pressure suction from the outlet 7a is performed. Thus, the liquid component (waste liquid) of the transfer liquid L5 separated from the carrier particle-antigen-enzyme complex is discharged from the second circulation flow path in a clockwise direction.

Next, as shown in FIG. 9, the non-shared flow path end valves W3 and W4 of the second circulation flow path 220 are opened, a substrate liquid L6 is introduced from the introduction flow path 224, and the second circulation flow path 220 is filled with the substrate liquid L6 (substrate liquid introduction process). Then, the carrier particle-antigen-enzyme complex captured by the second capture unit 4A reacts with the substrate liquid L6 by driving the pump P. Further, after the reaction is sufficiently completed, the substrate liquid L6 is discharged from the second circulation flow path 220 through the same procedure as the transfer liquid L5.

For example, when the enzyme is alkaline phosphatase (enzyme), the substrate liquid L6 contains 3-(2'-spiroadamantane)-4-methoxy-4-(3"-phosphoryloxy) phenyl-1, 2-dioxetane (AMPPD) or 4-aminophenyl phosphate (pAPP) as a substrate. The substrate liquid L6 reacts with the enzyme of the carrier particle-antigen-enzyme complex in the second circulation flow path 220. As the substrate liquid L6 and the carrier particle-antigen-enzyme complex are circulated in the second circulation flow path 220, the reaction with the enzyme of the carrier particle-antigen-enzyme complex is performed, and a metal can be deposited on the detection unit 3.

Next, as shown in FIG. 9, the non-shared flow path end valves W3 and W4 of the second circulation flow path 220 are opened, a measurement liquid L7 is introduced from the introduction flow path 225, and the second circulation flow path 220 is filled with the measurement liquid L7 (measurement liquid introduction process). The measurement liquid contains a strong electrolytic solution or the like as a material which serves to enhance a signal. Then, the measurement liquid L7 is circulated in the second circulation flow path 220 by driving the pump P, and an amount of metal deposited on the detection unit 3 is electrically analyzed by electrodes of the detection unit 3.

On the other hand, the auxiliary material detection unit 5 measures the excess labeling material captured in the first circulation process by coming into contact with the measurement liquid L7. The detection efficiency of the labeling material can be confirmed by checking a detection result in the auxiliary material detection unit 5.

In the embodiment, an amount of metal generated as a result of the reaction between the enzyme and the substrate has been detected. However, a color generated as a result of the reaction between the enzyme and the substrate may be detected in the detection unit.

Through the above-described procedure, the sample material can be detected by the fluidic device 300.

In the embodiment, the case in which the first reagent liquid L2 and the second reagent liquid L3 are sequentially introduced into each of the flow paths at the time of performing the detection has been described. However, the respective liquids may be introduced into the first circulation flow path 10 in advance.

Further, in the embodiment, the case in which the substrate liquid L6 and the measurement liquid L7 are each introduced and circulated as liquids (third liquids) which circulate in the second circulation flow path to perform the detection of the sample material and the detection is performed by the detection unit 3 has been exemplified. However, the third liquid may be one type of solution. Further, a plurality of constant-quantity sections may be provided in the second circulation flow path 220, and a liquid which is introduced, quantified, circulated and mixed in each of the sections may be used as the third liquid.

Furthermore, although the case in which the detection unit 3 of the embodiment is disposed to overlap the second capture unit 4A in the non-shared flow path 221 of the second circulation flow path 220 has been described, the detection unit 3 may be disposed to overlap the first capture unit 4. In this case, the detection unit 3 may be measured by sequentially introducing the substrate liquid L6 and the measurement liquid L7 as the second liquids in a state in which the carrier particle-antigen-enzyme complex is captured by the first capture unit 4.

According to the embodiment, the effects of the above-described first to fifth embodiments can be shown.

In the embodiment, in the first circulation flow path 210, a volume of the flow path (the non-shared flow path 211) which is not shared with the second circulation flow path 220 is larger than a volume of the flow path (the shared flow path 202) which is shared with the second circulation flow path 220. In the first circulation flow path 210, the mixed liquid of the specimen liquid and the reagent liquid may contain a foreign material unnecessary for detecting the sample material. This foreign material may remain on the inner wall of the flow path and may flow out into the liquid during the circulation in the second circulation flow path 220, and thus it becomes background noise in detection.

An amount of foreign material transferred into the second circulation flow path 220 can be reduced by reducing the volume of the shared flow path 202, and the detection accuracy can be enhanced. In the embodiment, a volume ratio of the non-shared flow path 211 to the shared flow path 202 is further increased by providing the meandering portion 219 in the non-shared flow path 211 of the first circulation flow path.

Further, in the embodiment, the volume of the first circulation flow path 210 is larger than the volume of the second circulation flow path 220. Therefore, a concentration of the sample material can be increased when the sample material is transferred from the first circulation flow path 210 to the second circulation flow path 220 including the detection unit 3, and the detection in the detection unit 3 can be facilitated, and the detection accuracy can be enhanced. In the embodiment, a volume ratio of the first circulation flow path 210 to the second circulation flow path 220 is further increased by providing the meandering portion 219 in the non-shared flow path 211 of the first circulation flow path.

According to the embodiment, the auxiliary material detection unit 5 is provided in the flow path (the shared flow path 202) which is shared by the first circulation flow path 210 and the second circulation flow path 220. The auxiliary material detection unit 5 can detect an excess detection auxiliary material (enzyme) captured during the circulation of the mixed liquid in the first circulation flow path 210 by bringing it into contact with the substrate liquid and the measurement liquid in the second circulation flow path 220. Accordingly, it is possible to measure the detection efficiency of the detection auxiliary material (enzyme) and to inspect a degree of deterioration, thereby ensuring the detection accuracy of the sample material in the detection unit 3.

[System]

As shown in FIG. 6, a system 207 in one embodiment of the present invention includes the fluidic device 300 and a control unit 208. The control unit 208 is connected to the valves provided in the fluidic device 300 via a connection line (not shown) and controls the opening and closing of the valves. According to the system 207 of the embodiment, the mixing, the capturing and the detection in the fluidic device 300 can be performed.

Seventh Embodiment

Figure 10:
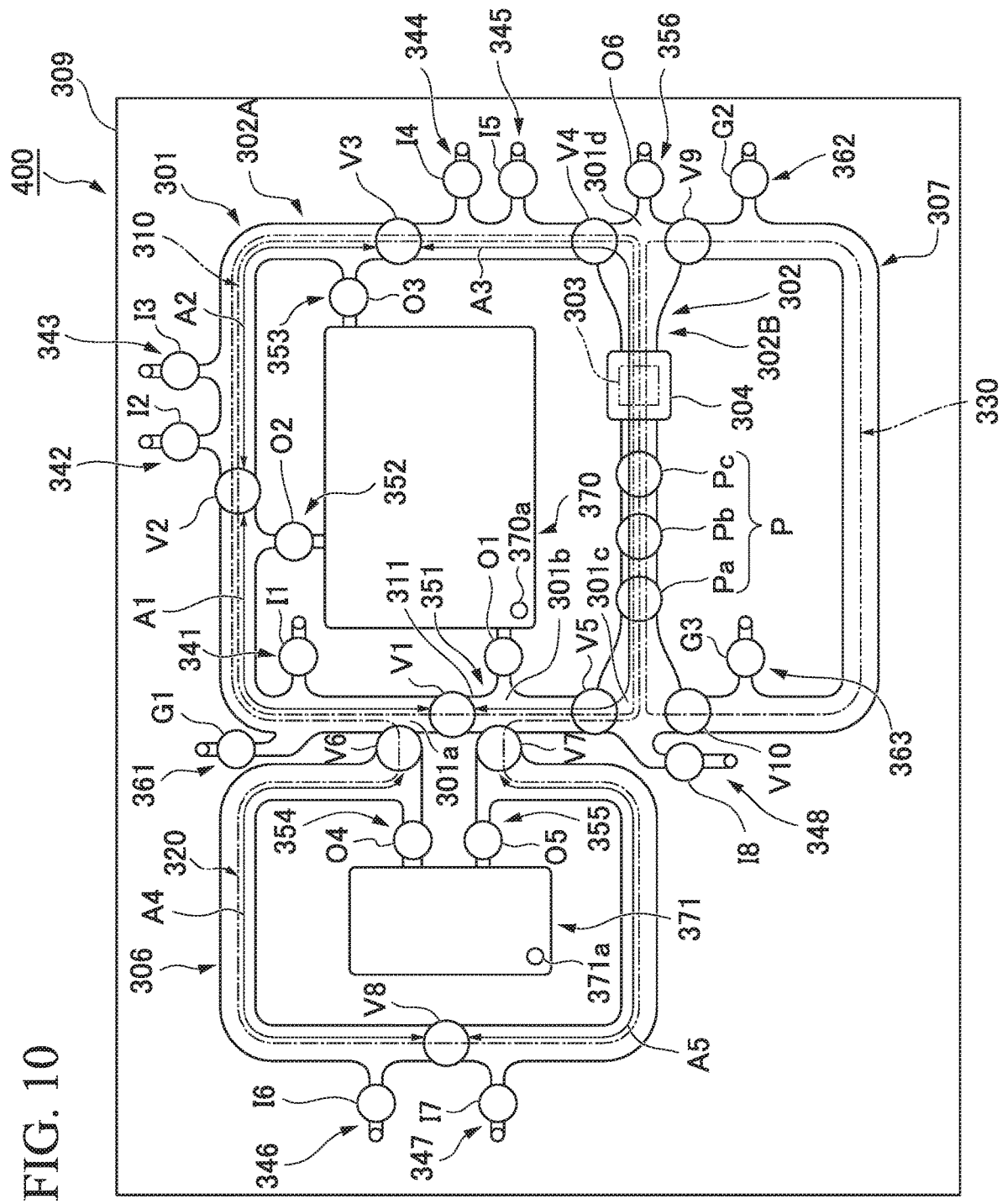
FIG. 10 is a plan view schematically showing a fluidic device according to a seventh embodiment.

FIG. 10 is a plan view schematically showing a fluidic device 400 according to a seventh embodiment. In the description of the embodiment, the same reference numerals are given to the same elements as those in the above-described embodiment, and descriptions thereof will be omitted.

The fluidic device 400 of the embodiment is a device which captures, detects or purifies a sample material to be detected contained in a specimen sample. The sample material is, for example, a biomolecule such as nucleic acid, DNA, RNA, peptide, protein, extracellular vesicle and so on. The fluidic device 400 is constituted with a substrate board 309 in which flow paths and valves are formed.

The flow paths formed in the substrate board 309 of the fluidic device 400 are classified into a loop flow path 301 formed in a loop shape, a first bypass flow path 306 which bypasses a pair of connecting portions 301a and 301b of the loop flow path 301, and a second bypass flow path 307 which bypasses a pair of connecting portions 301c and 301d of the loop flow path 301. A waste liquid tank 370 is provided inside the loop flow path 301. An outlet 370a is provided in the waste liquid tank 370. In addition, a waste liquid tank 371 is provided inside the first bypass flow path 306.

A first circulation flow path (a first circulation flow path) 310, a second circulation flow path (a second circulation flow path) 320, a third circulation flow path (a third circulation flow path) 330 in which a solution containing the sample material is circulated are included in the flow path formed by the loop flow path 301, the first bypass flow path 306 and the second bypass flow path 307.

That is, the fluidic device 400 includes the first circulation flow path 310, the second circulation flow path 320, and the third circulation flow path 330.

The first circulation flow path 310 is constituted with the loop flow path 301. That is, the first circulation flow path 310 includes the entire loop flow path 301.

The second circulation flow path 320 includes a part of the loop flow path 301, and the first bypass flow path 306. In the embodiment, a part of the loop flow path 301 included in the second circulation flow path 320 is one flow path having a long distance among two flow paths partitioned by the pair of connecting portions 301a and 301b in the loop flow path 301.

Also, the third circulation flow path 330 includes a part of the loop flow path 301, and the second bypass flow path 307. In the embodiment, a part of the loop flow path 301 included in the third circulation flow path 330 is one flow path having a short distance among two flow paths partitioned by the pair of connecting portions 301c and 301d in the loop flow path 301.

The first circulation flow path 310 and the second circulation flow path 320 have a first shared flow path (first shared flow path) 302A which is shared with each other. The first circulation flow path 310 and the third circulation flow path 330 have a second shared flow path (second shared flow path) 302B which is shared with each other. In addition, the first shared flow path 302A and the second shared flow path 302B share at least a part of the flow path (an overlapping shared flow path 302). In the embodiment, an entire length of the second shared flow path 302B overlaps an entire length of the overlapping shared flow path 302.

(First Circulation Flow Path)

The first circulation flow path 310 includes a non-shared flow path 311 which is not shared with both the second circulation flow path 320 and the third circulation flow path 330. The non-shared flow path 311 is one flow path having a short distance among the two flow paths partitioned by the pair of connecting portions 301a and 301b to which the first bypass flow path 306 is connected in the loop flow path 301.

A plurality of valves V1, V2, V3, V4 and V5 are provided in the first circulation flow path 310. Among the plurality of valves V1, V2, V3 and V4, the valves V1, V2 and V3 serve as metering valves, and the valves V4 and V5 serve as shared flow path end valves which partition the overlapping shared flow path 302 from other regions.

Further, a capture unit 304 and a pump P are disposed in the overlapping shared flow path 302 of the first circulation flow path 310.

The metering valves V1, V2 and V3 partition the first circulation flow path 310 into a first constant-quantity section A1, a second constant-quantity section A2, and a third constant-quantity section A3. That is, the metering valves V1, V2 and V3 are disposed so that each of the sections of the first circulation flow path 310 partitioned by the metering valves has a predetermined volume. More specifically, the first constant-quantity section A1 is formed between the metering valves V1 and V2. The second constant-quantity section A2 is formed between the metering valves V2 and V3. The third constant-quantity section A3 is formed between the metering valves V1 and V3.

An introduction flow path 341, a discharge flow path 352 and an air flow path 361 are connected to the first constant-quantity section A1 of the first circulation flow path 310. Introduction flow paths 342 and 343 and a discharge flow path 353 are connected to the second constant-quantity section A2. Introduction flow paths 344, 345, and 348, a discharge flow path 351 and a discharge flow path (recovery flow path) 356 are connected to the third constant-quantity section A3. In particular, the introduction flow path 348 and the discharge flow path 356 are disposed at both ends of the overlapping shared flow path 302 in the third constant-quantity section A3.

The shared flow path end valves V4 and V5 partition the first circulation flow path 310 into the overlapping shared flow path 302 and other regions. The shared flow path end valves V4 and V5 are located at both ends of the overlapping shared flow path 302 in the first circulation flow path 310. Both the shared flow path end valves V4 and V5 are located in the third constant-quantity section A3. The entire region of the overlapping shared flow path 302 is included in the third constant-quantity section A3 of the first circulation flow path 310.

(Second Circulation Flow Path)

The second circulation flow path 320 has the first shared flow path 302A which is shared with the first circulation flow path 310, and the first bypass flow path 306 which is not shared with the first circulation flow path 310.

The above-described valves V1, V2, V3, V4 and V5 are provided in the first shared flow path 302A. In addition, a part of the first shared flow path 302A overlaps the overlapping shared flow path 302.

Therefore, the first shared flow path 302A has the capture unit 304 and the pump P. The introduction flow paths 341, 342, 343, 344, 345 and 348, the discharge flow paths 351, 352, 353 and 356 and the air flow path 361 are connected to the first shared flow path 302A.

A plurality of valves V6, V7 and V8 are provided in the first bypass flow path 306. Among the plurality of valves V6, V7 and V8, the valves V6 and V7 serve as first bypass flow path end valves which are located at ends of the first bypass flow path 306 and partition the first bypass flow path 306 and the first shared flow path 302A from each other. In addition, the valve V8 serves as a metering valve. The metering valve V8 partitions the first bypass flow path 306 into two regions having a predetermined volume. In the first bypass flow path 306, a fourth constant-quantity section A4 is formed between the metering valve V8 and the first bypass flow path end valve V6. In the first bypass flow path 306, a fifth constant-quantity section A5 is formed between the metering valve V8 and the first bypass flow path end valve V7. An introduction flow path 346 and a discharge flow path 354 are each connected to the vicinity of both ends of the fourth constant-quantity section A4. Similarly, an introduction flow path 347 and a discharge flow path 355 are each connected to the vicinity of both ends of the fifth constant-quantity section A5.

(Third Circulation Flow Path)

The third circulation flow path 330 has a second shared flow path 302B which is shared with the first circulation flow path 310, and a second bypass flow path 307 which is not shared with the first circulation flow path 310.

As described above, the entire second shared flow path 302B is coincident with the entire overlapping shared flow path 302. Therefore, the capture unit 304 and the pump P are disposed in the second shared flow path 302B. Further, in the third circulation flow path 330, valves V9 and V10 are provided at both ends of the second shared flow path 302B. The valves V9 and V10 serve as shared flow path end valves. That is, the shared flow path end valves V9 and V10 partition the third circulation flow path 330 into the second shared flow path 302B and the second bypass flow path 307.

Air flow paths 362 and 363 are each connected to the vicinity of both ends of the second bypass flow path 307.

(Introduction Flow Path)

The introduction flow paths 341 to 348 are provided to introduce different liquids into the first circulation flow path 310, the second circulation flow path 320, or the third circulation flow path 330. Introduction flow path valves I1 to I8 which open and close the introduction flow paths are provided in the introduction flow paths 341 to 348, respectively. Further, a liquid introduction inlet which opens on the surface of the substrate board 309 is provided at an end of each of the introduction flow paths 341 to 348.

(Discharge Flow Path)

The discharge flow paths 351 to 356 are provided to discharge the liquid from the first circulation flow path 310, the second circulation flow path 320, or the third circulation flow path 330. Discharge flow path valves O1 to O6 which open and close the discharge flow paths are provided in the discharge flow paths 351 to 356, respectively. Among the discharge flow paths 351 to 356, the discharge flow path 356 connected to one end of the overlapping shared flow path 302 serves as a recovery flow path which recovers the reacted liquid. Therefore, a recovery tank (not shown) is connected to an end of the discharge flow path (recovery flow path) 356. The other discharge flow paths 351 to 355 are connected to the waste liquid tanks 371 and 372. Outlets 371a and 372a which open on the surface of the substrate to be connected to an external suction pump (not shown) and to perform the negative pressure suction are provided in the waste liquid tanks 371 and 372.

(Air Flow Path)

The air flow paths 361 to 363 are provided to discharge or introduce air from the first circulation flow path 310. Air flow path valves G1, G2 and G3 which open and close the flow path are provided in the air flow paths 361 to 363. An air introduction inlet which opens on the surface of the substrate board 309 is provided at an end of each of the air flow paths 361 to 363. Among the air flow paths 361 to 363, the air flow path 363 serves as an air discharge flow path for suctioning air. The other air flow paths 361 and 362 serve as air introduction flow paths for introducing air into the flow path and extruding the liquid in the flow path.

(Purification Method)

Next, a method of purifying a sample material using the fluidic device 400 of the embodiment will be described. The detection method of the embodiment detects a nucleic acid to be detected contained in a specimen sample.

First, the metering valves V1, V2 and V3 of the first circulation flow path 310, the valves V6 and V7 located at the ends of the first bypass flow path 306, and the valves V9 and V10 located at the ends of the second bypass flow path 307 are closed. Therefore, the first circulation flow path 310 is partitioned into the first constant-quantity section A1, the second constant-quantity section A2 and the third constant-quantity section A3.

Figure 11:
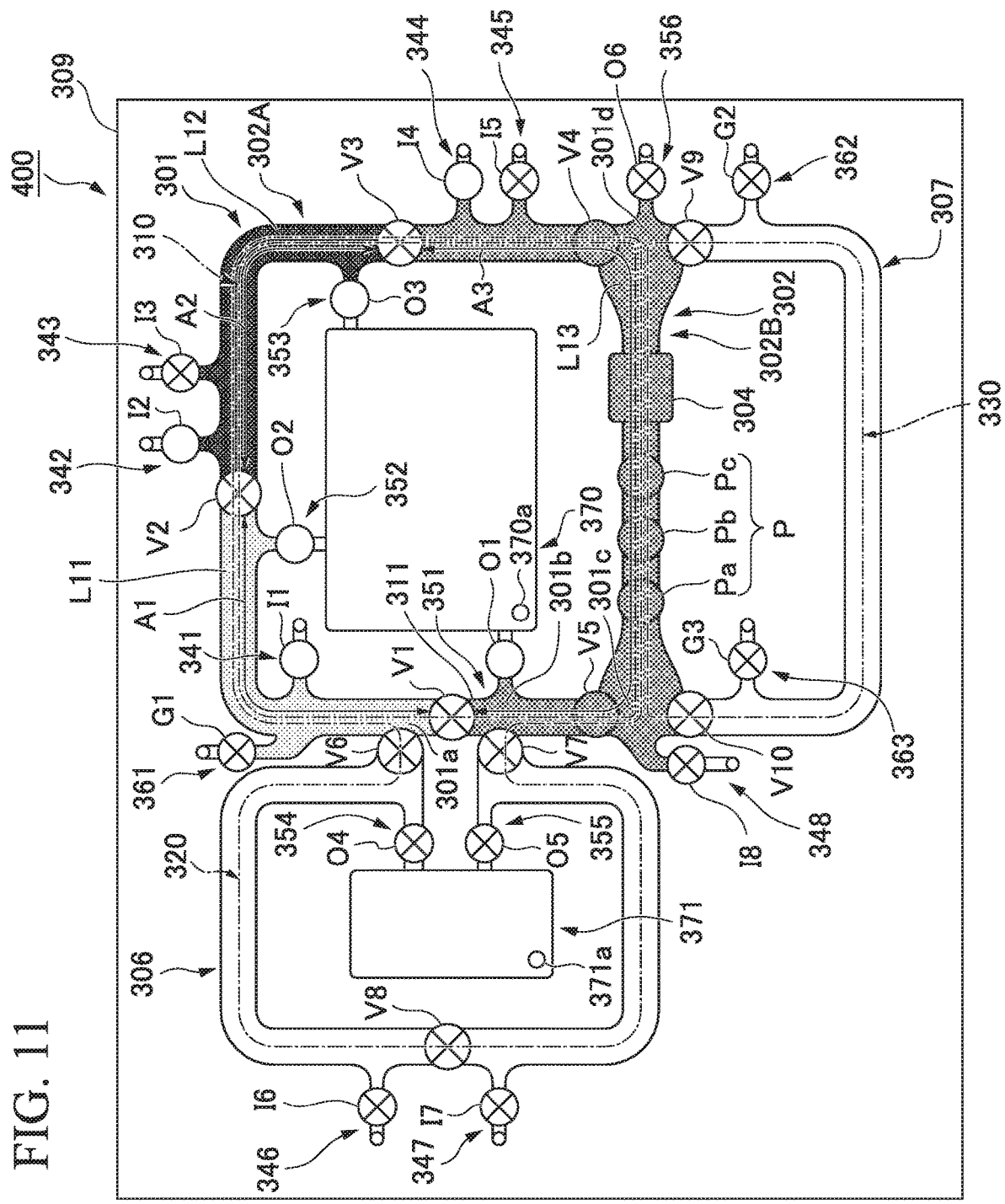
FIG. 11 is a view showing a process in which the specimen liquid, the first reagent liquid and the second reagent liquid are introduced into the first circulation flow path in a purification method using the fluidic device of the seventh embodiment.

Then, as shown in FIG. 11, a specimen liquid (first liquid) L11 containing a sample material is introduced from the introduction flow path 341 into the first constant-quantity section A1, a first reagent liquid L12 is introduced from the introduction flow path 342 into the second constant-quantity section A2, and a second reagent liquid (second liquid) L13 is introduced from the introduction flow path 344 into the third constant-quantity section A3. The first reagent liquid L12 and the second reagent liquid L13 may be respectively filled in the second constant-quantity section A2 and the third constant-quantity section A3 in advance.

In the embodiment, the specimen liquid L11 is blood, serum or plasma and includes a nucleic acid as a sample material.

The first reagent liquid L12 and the second reagent liquid L13 are pretreatment liquids. In the embodiment, the case in which two types of pretreatment liquids (the first reagent liquid L12 and the second reagent liquid L13) are used has been exemplified, but one or more pretreatment liquids may be used.

In the embodiment, the first reagent liquid L12 is, for example, a solution of proteinase K. The proteinase K inactivates an enzyme (nuclease) which decomposes the nucleic acid. Therefore, it is possible to prevent the nucleic acid extracted from the specimen liquid L11 from being decomposed by an action of the enzyme.

In the embodiment, the second reagent liquid L13 contains a dissolution solution for extracting the nucleic acid from blood, serum or plasma contained in the specimen liquid L11.

Figure 12:
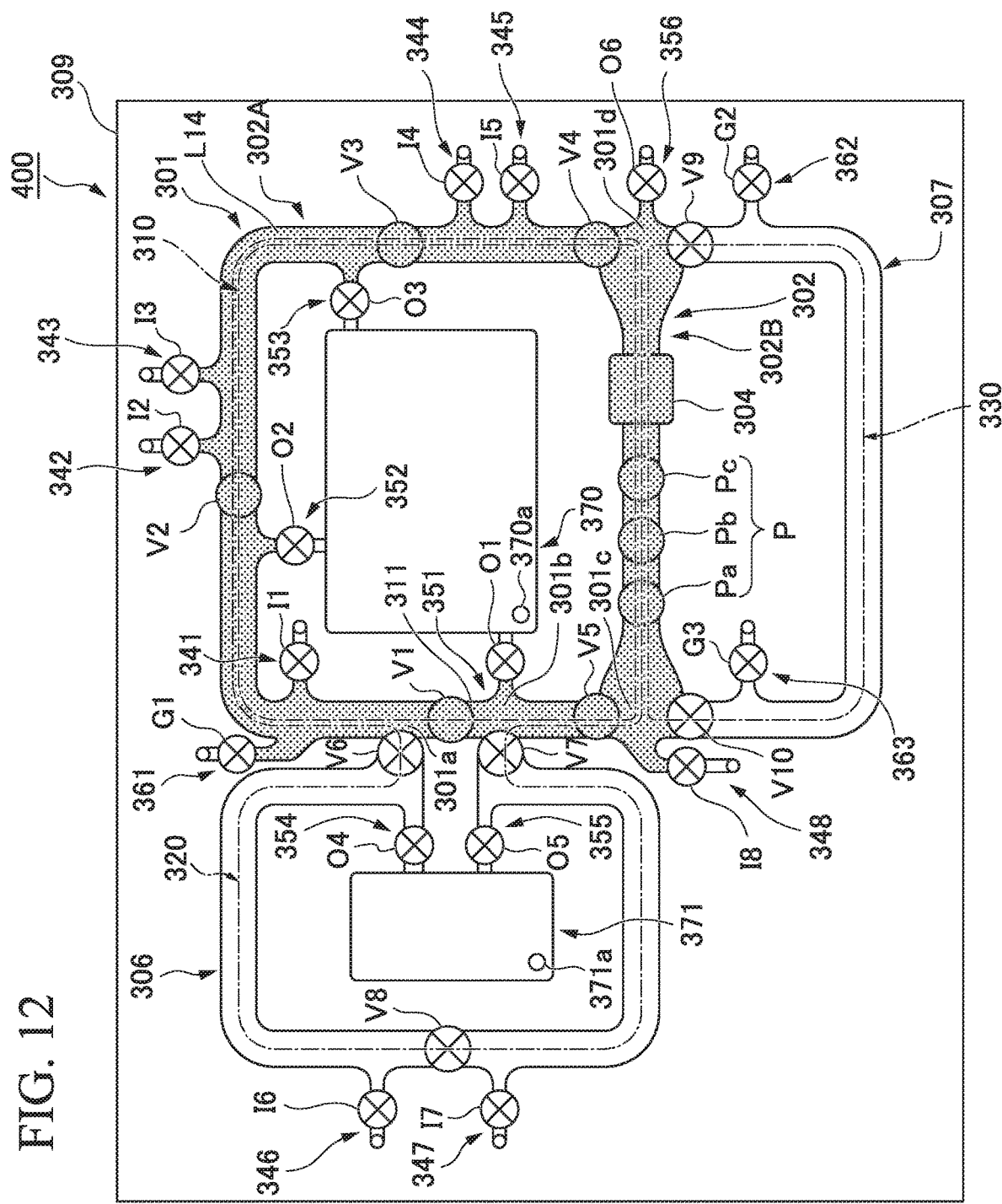
FIG. 12 is a view showing a process in which a first mixed liquid is obtained by circulating and mixing the specimen liquid, the first reagent liquid and the second reagent liquid in the first circulation flow path in the purification method using the fluidic device of the seventh embodiment.

Then, as shown in FIG. 12, the specimen liquid L11, the first reagent liquid L12 and the second reagent liquid L13 are circulated and mixed in the first circulation flow path 310 by opening the valves V1, V2 and V3, making the first circulation flow path 310 a continuous loop and then driving the pump P, and thus a first mixed liquid L14 is obtained. The nucleic acid which is the sample material is extracted by the mixing of the specimen liquid L11, the first reagent liquid L12 and the second reagent liquid L13.

Figure 13:
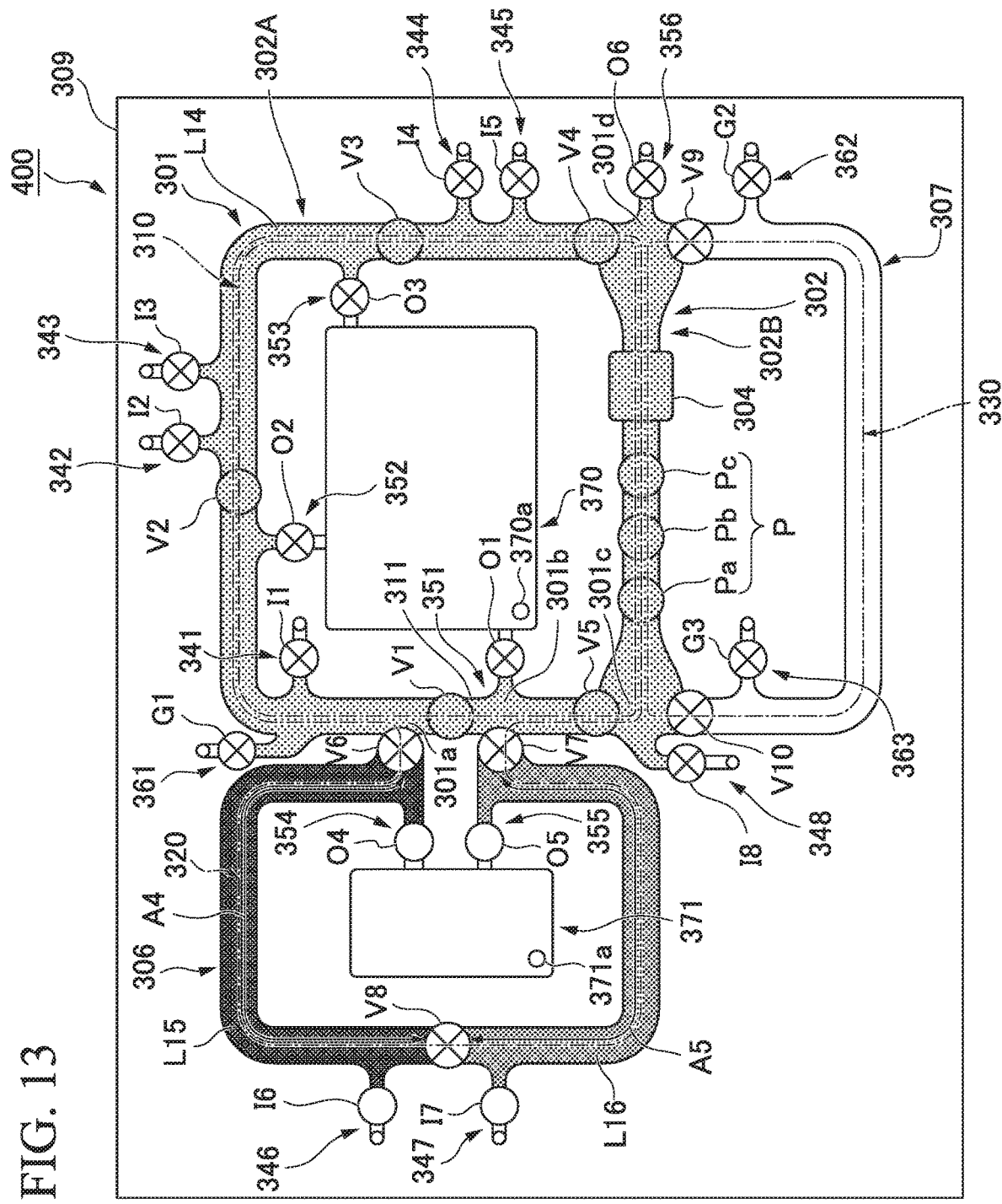
FIG. 13 is a view showing a process in which a third reagent liquid and a fourth reagent liquid are introduced into the second circulation flow path in the purification method using the fluidic device of the seventh embodiment.

Then, as shown in FIG. 13, the V6, V7 and V8 of the second circulation flow path 320 are closed so that second circulation flow path 320 is partitioned into the fourth constant-quantity section A4 and the fifth constant-quantity section A5. Next, a third reagent liquid (third liquid) L15 containing the carrier particles which are bound to the sample material is introduced from the introduction flow path 346 into the fourth constant-quantity section A4, and the fourth reagent liquid L16 is introduced from the introduction flow path 347 into the fifth constant-quantity section A5. The third reagent liquid L15 and the fourth reagent liquid L16 may be filled in the fourth constant-quantity section A4 and the fifth constant-quantity section A5 in advance, respectively.

In the embodiment, magnetic particles (silica magnetic particles as an example) are used as the carrier particles contained in the third reagent liquid (third liquid) L15. The silica magnetic particles are bound (attached) to the nucleic acid (the sample material) in alcohol.

In the embodiment, the fourth reagent liquid L16 is, for example, an isopropanol solution. Isopropanol creates an alcoholic environment and forms an environment in which the magnetic particles can be bound to the nucleic acid.

Figure 14:
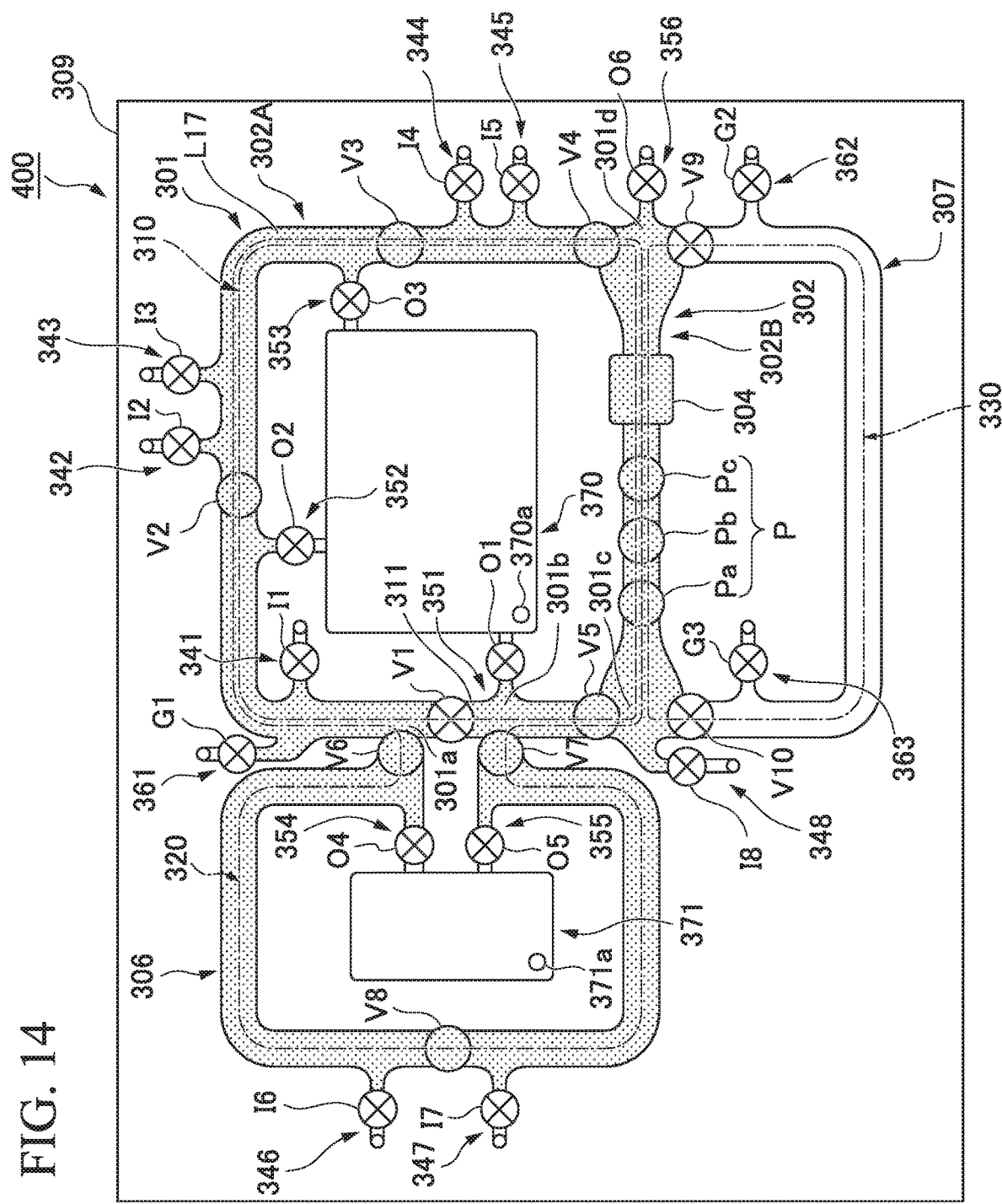
FIG. 14 is a view showing a process in which a second mixed liquid is obtained by circulating and mixing the first mixed liquid, the third reagent liquid and the fourth reagent liquid in the second circulation flow path in the purification method using the fluidic device of the seventh embodiment.

Then, as shown in FIG. 14, the valves V6, V7 and V8 are opened and the valve V1 is closed to make the second circulation flow path 320 a continuous loop, and then the pump P is driven.

Therefore, the first mixed liquid L14, the third reagent liquid L15 and the fourth reagent liquid L16 are circulated and mixed in the first circulation flow path 310, and thus a second mixed liquid L17 is obtained. Thus, the magnetic particles (the carrier particles) are bound to the nucleic acid (the sample material) contained in the first mixed liquid L14, and thus a complex of the sample material and the carrier particles is formed.

Further, in a state in which the second mixed liquid L17 is circulated in the second circulation flow path 320 after the binding between the nucleic acid and the magnetic particles has sufficiently progressed, a magnet for capturing the magnetic particles is brought close to the flow path in the capture unit 304. Accordingly, the capture unit 304 captures the complex of the sample material and the carrier particles.

Then, although illustration of the process is omitted, the valves V1 and V7 are closed, the air flow path valve G1 of the air flow path 361 is opened, and the valve O5 of the discharge flow path 355 is opened. Also, the liquid component (waste liquid) separated from the nucleic acid to which the magnetic particles are bound is discharged from the second circulation flow path to the waste liquid tank 371 due to the negative pressure suction from the outlet 371a of the waste liquid tank 371. Thus, the second mixed liquid L17 is removed from the overlapping shared flow path 302, and the complex of the sample material and the carrier particles captured by the capture unit 304 is separated from the liquid component.

Next, although illustration of the process is omitted, the valves V6 and V7 are closed to make the first circulation flow path 310 a continuous closed loop, and then the washing liquid is introduced from the introduction flow path 343 or the introduction flow path 345 to fill the first circulation flow path 310 with the washing liquid. Also, the washing liquid is circulated in the first circulation flow path 310 by driving the pump P, and the complex of the nucleic acid and the magnetic particles captured by the capture unit 304 is washed. Furthermore, after the circulation of the washing liquid for a certain period of time is completed, the washing liquid is discharged to the waste liquid tank 370.

The cycle of introduction, circulation and discharge of the washing liquid may be performed a plurality of times. Removal efficiency of unnecessary materials can be enhanced by repeatedly performing the introduction, circulation and discharge of the washing liquid.

Also, in the embodiment, the case in which the washing liquid is circulated in the first circulation flow path 310 has been exemplified. However, the washing may be performed by circulating the washing liquid in the second circulation flow path 320.

Figure 15:
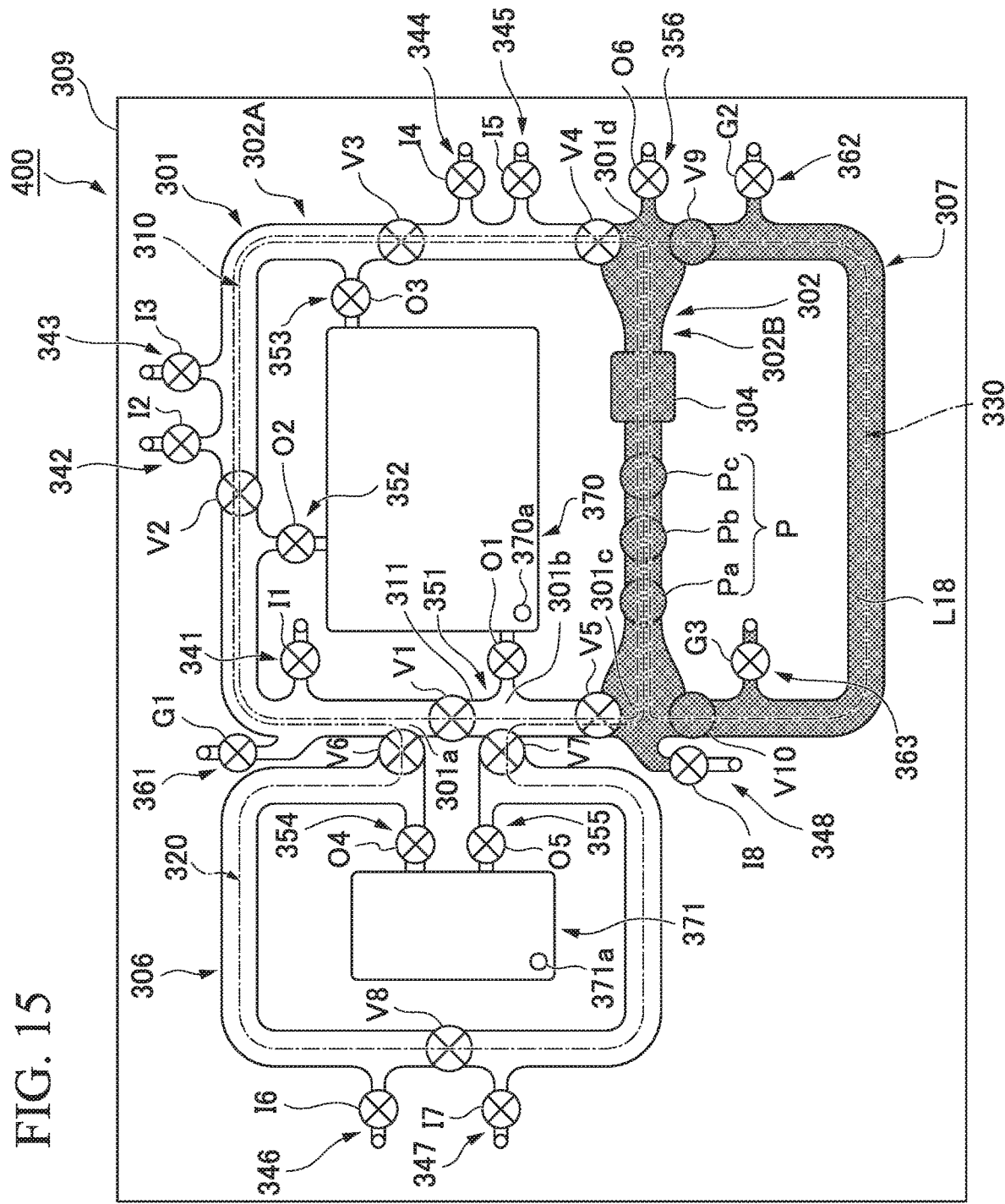
FIG. 15 is a view showing a process in which a fifth reagent liquid is circulated in the second circulation flow path in the purification method using the fluidic device of the seventh embodiment.

Next, as shown in FIG. 15, the shared flow path end valves V4 and V5 are closed, the shared flow path end valves V9 and V10 are opened, the third circulation flow path 330 is formed as a continuous loop, and then the fifth reagent liquid L18 containing an eluate is introduced from the introduction flow path 348 to fill the third circulation flow path 330 with the fifth reagent liquid L18.

In the embodiment, the eluate contained in the fifth reagent liquid L18 is, for example, water. As described above, the silica magnetic particles bind to the nucleic acid in alcohol but do not bind thereto in water. Therefore, it is possible to elute the nucleic acid from the magnetic particles by immersing the nucleic acid to which the magnetic particles are bound in water. Also, the fifth reagent liquid L18 may be a solution suitable for preservation of the sample material or a solution suitable for a next process using the sample material, and for example, the water contained in the fifth reagent liquid L18 of the embodiment is a liquid which is suitable both for preservation of the nucleic acid and for the next process.

Next, the capturing of the complex of the nucleic acid and the magnetic particles in the capture unit 304 is canceled, and the fifth reagent liquid L18 is circulated in the third circulation flow path 330 by driving the pump P.

Then, the magnetic particles are captured again in the capture unit 304. Therefore, the magnetic particles are removed from the liquid, and thus only the nucleic acid remains in the liquid.

The nucleic acid may be eluted from the magnetic particles by circulating the fifth reagent liquid L18 in the third circulation flow path 330 without canceling the capturing of the magnetic particles in the capture unit 304.

The sample material can be purified by the fluidic device 300 through the above-described procedure.

Modified Example of the Seventh Embodiment

Next, a modified example applicable to the seventh embodiment will be described. This modified example is different from the seventh embodiment mainly in that the detection unit 303 (two-dot chain line in FIG. 10) is additionally provided together with the capture unit 304.

The detection unit 303 is disposed to overlap the capture unit 304. The detection unit 303 is provided for detecting the sample material.

In the fluidic device of this modified example, like the purification method of the seventh embodiment, the second mixed liquid L17 (FIG. 14) is discharged, the complex of the sample material and the carrier particles captured by the capture unit 304 is separated from the liquid component, then a liquid (third liquid) for performing the detection of the sample material is introduced and circulated in the second circulation flow path 320, and the detection can be performed in the detection unit 303.

Further, in this case, the detection unit 303 may perform the detection of the sample material in a state in which the sample material is released from the capture unit 304 or may perform the detection of the sample material without releasing the sample material from the capture unit 304.

Although the various embodiments of the present invention have been described above, the respective constitutions and combinations thereof in each embodiment are examples, and additions, omissions, substitutions, and other changes to the constitution can be made without departing from the spirit of the present invention. Further, the present invention is not limited by the embodiments.

What is claimed is:

1. A fluidic device, comprising:
a first circulation flow path having a looped shape;
a bypass flow path having ends that are connected to first and second positions of the first circulation flow path, respectively;
one first valve that is disposed between the first and second positions of the first circulation flow path;
second and third valves that are disposed at the ends of the bypass flow path, respectively;
a first introduction flow path and a first discharge flow path that are directly connected to the first circulation flow path;
a second introduction flow path and a second discharge flow path that are directly connected to the bypass flow path; and
a pump that is disposed on the first circulation flow path.

2. The fluidic device according to claim 1,
wherein the second and third valves are disposed in a vicinity of the first valve, and
a second circulation flow path is formed by driving the pump in a state where the first valve is closed and the second and third valves are opened.

3. The fluidic device according to claim 1, comprising:
a capture unit that is disposed on the first circulation flow path,
wherein the capture unit captures a sample material contained in a mixed solution in which a solution introduced to the first circulation flow path and a solution introduced to the bypass flow path are mixed.

4. The fluidic device according to claim 3, comprising:
a detection unit that is disposed on the first circulation flow path,
wherein the detection unit detects the sample material captured by the capture unit.

5. The fluidic device according to claim 4,
wherein the detection unit detects a sample material bound to a detection auxiliary material, and
an auxiliary material detection unit which detects the detection auxiliary material is provided on the flow path shared by the first circulation flow path and the second circulation flow path.

6. The fluidic device according to claim 1,
wherein the pump comprises at least three pump valves.

7. The fluidic device according to claim 1,
wherein each of the first circulation flow path and the second circulation flow path has two or more metering valves, and each of the metering valves is disposed so that each of sections of the first and second circulation flow paths partitioned by the metering valves has a predetermined volume.

8. The fluidic device according to claim 7,
wherein at least one introduction flow path and at least one discharge flow path are connected to each of the first circulation flow path and the second circulation flow path, and
the introduction flow path and the discharge flow path are formed so that an individual solution is capable of being introduced into each of the sections of the first and second circulation flow paths partitioned by the metering valves.

9. The fluidic device according to claim 8,
wherein at least one introduction flow path and at least one discharge flow path are connected to all of the sections of the first and second circulation flow paths partitioned by the metering valves.

10. The fluidic device according to claim 2,
further comprising a capture unit to capture a sample material bound to a carrier particle.

11. The fluidic device according to claim 10,
wherein a magnet constituted to be capable of controlling a magnetic force is capable of being disposed in a vicinity of the capture unit.

12. A system comprising
fluidic device according to claim 1, and a control unit which controls opening and closing of a valve.

13. A method of purifying a sample material using a fluidic device which comprises:
a first circulation flow path having a looped shape;
a bypass flow path having ends that are connected to first and second positions of the first circulation flow path, respectively;
one first valve that is disposed between the first and second positions of the first circulation flow path;
second and third valves that are disposed at the ends of the bypass flow path, respectively;
a first introduction flow path and a first discharge flow path that are directly connected to the first circulation flow path;
a second introduction flow path and a second discharge flow path that are directly connected to the bypass flow path;
a pump that is disposed on the first circulation flow path; and
a capture unit that is disposed on the first circulation flow path and captures a sample material contained in a mixed solution in which a solution introduced to the first circulation flow path and a solution introduced to the bypass flow path are mixed, the method comprising:
introducing a first liquid containing the sample material into the first circulation flow path;
introducing a second liquid containing a carrier particle to be bound to the sample material into the bypass flow path;
circulating and mixing the first liquid and the second liquid in a second circulation flow path formed by closing the first valve and opening the second and third valves, and obtaining a mixed liquid; and
capturing, by the capture unit, a complex of the sample material and the carrier particle from the mixed liquid.

14. The method according to claim 13, further comprising:
removing the mixed liquid from the second circulation flow path after the capturing by the capture unit; and
introducing a third liquid to be mixed with the complex captured by the capture unit.

15. The method according to claim 14,
wherein the sample material is a nucleic acid,
the carrier particle is a silica magnetic particle, and
the capture unit captures the carrier particle by a magnet.

16. The method according to claim 13,
wherein each of the first circulation flow path and the second circulation flow path is partitioned into a plurality of sections each having a predetermined volume by a valve, and a liquid is quantified by introducing the liquid into each of the sections.

17. The method according to claim 13, further comprising:
detecting the sample material.

18. A fluidic device, comprising:
a circulation flow path which circulates a solution containing a sample material; and
a merging branching portion that is connected to the circulation flow path,
wherein the merging branching portion is a space which has a lower surface and an upper surface having a triangle shape, and a valve that adjusts a flow of a fluid in a flow path is provided on one of at least two apexes of the triangle.

* * * * *